US005965354A

United States Patent [19]
Burke et al.

[11] Patent Number: 5,965,354
[45] Date of Patent: Oct. 12, 1999

[54] HERPES SIMPLEX VIRUS DIAGNOSTICS

[75] Inventors: Rae Lyn Burke; D'Anna Alexander, both of San Francisco, Calif.

[73] Assignee: Chiron Corporation, Emeryville, Calif.

[21] Appl. No.: 08/613,235

[22] Filed: Mar. 8, 1996

Related U.S. Application Data

[63] Continuation-in-part of application No. 08/508,598, Jul. 28, 1995, abandoned.

[51] Int. Cl.$^6$ .............................. C12Q 1/70; G01N 33/53
[52] U.S. Cl. ................................ 435/5; 435/7.1; 435/7.9; 435/7.92; 435/69.1; 435/975; 424/229.1; 424/231.1; 424/204.1; 436/518; 436/530; 530/395
[58] Field of Search ................................ 435/5, 7.1, 7.9, 435/7.92, 975, 69.1; 424/229.1, 231.1, 204.1; 436/518, 530; 530/395

[56] References Cited

U.S. PATENT DOCUMENTS

| 5,149,660 | 9/1992 | Cohen et al. | 436/87 |
| 5,244,792 | 9/1993 | Burke et al. | 435/69.3 |

FOREIGN PATENT DOCUMENTS

| WO90/13652 | 11/1990 | WIPO . |
| 9202251 | 2/1992 | WIPO . |

OTHER PUBLICATIONS

Alexander et al., "Recombinant–Truncated gG1 and gG2 as Antigens for a Type–Specific Serological Assay to Diagnose Prior Infection with HSV1 or HSV2," Abstract presented at the International Herpesvirus Workshop in Vancouver, Canada, Jul. 30, 1994–Aug. 5, 1994.

Ashley, R.L., et al., "Comparison of Western Blot (Immunoblot) and Glycoprotein G–Specific Immunodot Enzyme Assay for Detecting Antibodies to Herpes Simplex Virus Types 1 and 2 in Human Sera" *J. Clin. Microbiol.* (1988) 26:662–667.

Ashley, R., et al., "Inability of Enzyme Immunoassays to Discriminate between Infections with Herpes Simplex Virus Types 1 and 2" *Annals Inter. Med.* (1991) 115:520–526.

"Diagnostic Update" *The Helper* (Spring 1995) 17:1–12.

Field, P.R., et al., "The Reliability of Serological Tests for the Diagnosis of Genital Herpes: A Critique" *Pathol.* (1993) 25:175–179.

Goade, D., et al., "Epitopes of Herpes Simplex Virus Type 2 Glycoprotein B that are Recognized by Human Antibodies: Type Specific and Cross Reactive Regions" *Abstracts of the 34th Interscience Conference on Antimicrobial Agents and Chemotherapy,* (Oct. 4–7, 1994) Abstract H6; This abstract was also presented at the International Herpes Virus Workshop, Vancouver, B.C. Canada, Jul. 30–Aug. 5, 1995.

Lee, F.K., et al., "Detection of Herpes Simplex Virus Type 2–Specific Antibody with Glycoprotein G" *J. Clin. Microbiol.* (1985) 22:641–644.

Lee, F.K., et al., "A novel glycoprotein for detection of herpes simplex virus type 1–specific antibodies" *J. Virol. Meth.* (1986) 14:111–118.

McGeoch, D.J., et al., "DNA Sequence and Genetic Content of the HindIII /Region in the Short Unique Component of the Herpes Simplex Virus Type 2 Genome: Identification of the Gene Encoding Glycoprotein G, and Evolutionary Comparisons" *J. Gen. Virol.* (1987) 68:19–38.

Parkes, D.L., et al., "Seroreactive Recombinant Herpes Simplex Virus Type 2–Specific Glycoprotein G" *J. Clin. Microbiol.* (1991) 29(4):778–781.

Pereira, Lenore et al., "Domain Structure of Herpes Simplex Virus 1 Glycoprotein B: Neutralizing Epitopes Map in Regions of Continuous and Discontinuous Residues," *Virology* (1989) 172:11–24.

Qadri, Ishtiaq et al., "Mutations in Conformation–Dependent Domains of Herpes Simplex Virus 1 Glycoprotein B Affect the Antigenic Properties, Dimerization, and Transport of the Molecule," *Virology* (1991) 180:135–152.

Sanchez–Martinez, D., et al., "Evaluation of a Test Based on Baculovirus–Expressed Glycoprotein G for Detection of Herpes Simplex Virus Type–Specific Antibodies" *J. Infect. Dis.* (1991) 164:1196–1199.

*Primary Examiner*—Mary E. Mosher
*Assistant Examiner*—Ali R. Salimi
*Attorney, Agent, or Firm*—Robins & Associates; Alisa A. Harbin; Robert P. Blackburn

[57] ABSTRACT

Novel methods and immunodiagnostic test kits for diagnosing herpes simplex virus (HSV) infection are disclosed. The methods and kits employ both type-specific and type-common antigens, in a single-step assay format, to provide for highly accurate results. The methods discriminate between HSV-1 and HSV-2 infection so that an accurate diagnosis can be performed.

46 Claims, 6 Drawing Sheets

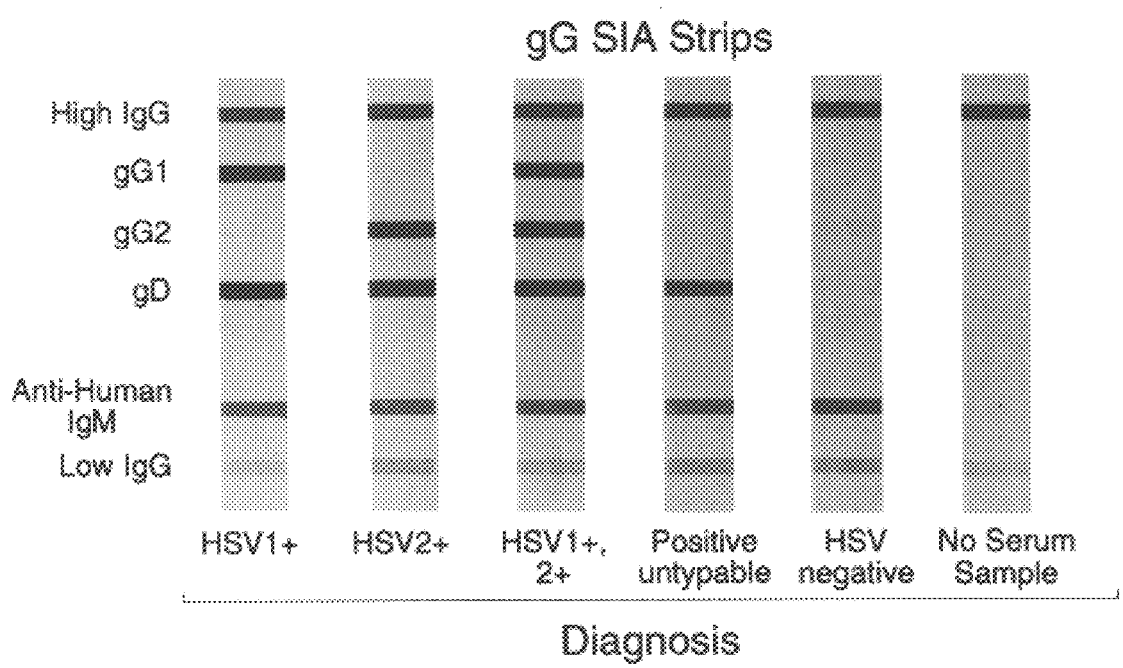

SOD/HSV2gG2R-D
(80.8 kD, S.cerevisiae)

SOD/HSV2gG2-Nterm
(50.9 kD, S.cerevisiae)

SOD/HSV2gG2-Cterm
(46.3 kD, S.cerevisiae)

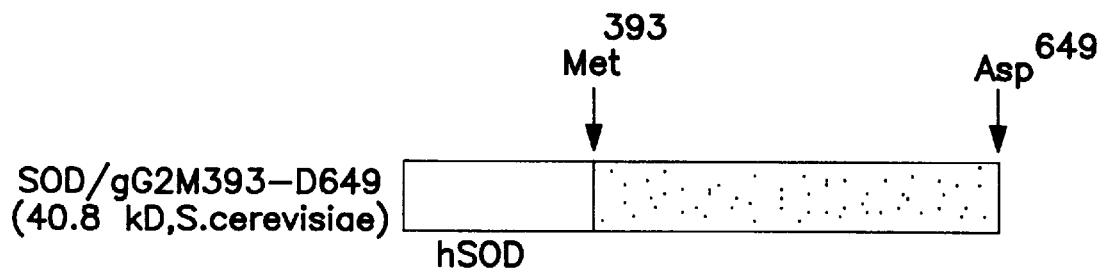
FIG. 3G
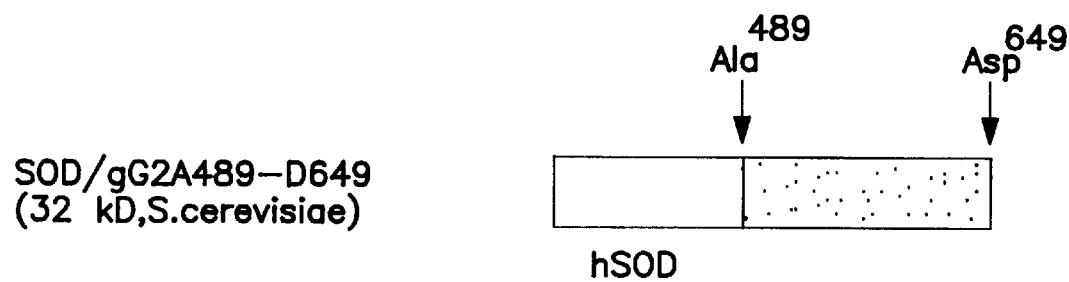
FIG. 3H
APSSPGTPGVAAATQAANGGPATPAPPALGAAPTGDPKPKKNKKPK
1          10         20        30          40
FIG. 4

HERPES SIMPLEX VIRUS DIAGNOSTICS

CROSS-REFERENCE TO RELATED APPLICATION

This is a continuation-in-part application of pending application Ser. No. 08/508,598, filed Jul. 28, 1995, now abandoned, from which priority is claimed pursuant to 35 USC §120 and which is incorporated herein by reference in its entirety.

BACKGROUND OF THE INVENTION

TECHNICAL FIELD

The present invention pertains generally to viral diagnostic techniques. In particular, the invention relates to methods for accurately detecting herpes simplex virus infection.

BACKGROUND OF THE INVENTION

Herpes simplex virus ("HSV") infections are extremely prevalent and have a range of manifestations from apparently asymptomatic acquisition to severe disease and life threatening infections in the immunocompromised individual and the neonate. These infections are caused by two viruses, herpes simplex virus type 1 ("HSV-1") and herpes simplex virus type 2 ("HSV-2"). HSV-1 is the predominant cause of oral infections and is usually acquired in childhood, whereas HSV-2 infections are usually sexually transmitted genital infections. These distinctions are blurred, however, and up to 25% of genital herpes is caused by HSV-1. Following initial infection, the virus establishes a life long latent state and periodically reactivates, causing clinically apparent lesional episodes or asymptomatic virus shedding.

In general, HSV is a double-stranded DNA virus having a genome of about 150–160 kbp packaged within an icosahedral nucleocapsid enveloped in a membrane. The membrane (or envelope) includes 10 or more virus-specific glycoproteins, the most abundant of which are gB, gC, gD, and gE. The viral genome also encodes over 50 other proteins including the tegument protein VP16. The viral genomes of HSV-1 and HSV-2 are colinear and share 50% homology over the entire genome. For some genes, such as gB and gD, the amino acid identity between the two virus types increases up to as much as 80 to 90%. As a result of this similarity, many HSV-specific antibodies are cross-reactive for both virus types. Within a virus type, there is a limited (1 to 2%) strain-to-strain sequence variability of the glycoprotein genes. Strains of HSV include, but are not limited to, 333 and Patton.

Despite the availability the antiviral agent, acyclovir, for HSV, the incidence of HSV-2 in the population ranges from 8–50% and is increasing. The apparent reason for this increase is that most individuals are unaware of their infection. Moreover, the majority of transmission occurs from virus shed asymptotically.

Several assays have been developed for the diagnosis of HSV infection. These assays, unfortunately, suffer from several drawbacks. The most commonly used assay involves a viral culture. A significant sample of virus can only be obtained early in the lesion stage of infection. However, many individuals have had prior herpes infections but are asymptomatic. Such individuals can shed virus asymptomatically, without having active lesions, and infection would not be detectable using viral culture. Thus, detection of HSV by viral culture has a high rate of false negatives, as high as about 50% for recurrent herpes episodes. Additionally, culture of the virus is slow, making this method of diagnosis unusable in potentially serious situations where quick results are necessary, such as just prior to delivery of an infant or illness in a newborn. Furthermore, the culture is expensive and viral samples may degrade during transport to the laboratory. An additional test must be conducted to determine whether the HSV infection is HSV-1 or HSV-2.

Antigen detection tests provide an alternative to viral culture. However, like viral culture, these tests require samples from active lesions and therefore have a high rate of false negatives, e.g., in the case of asymptomatic infection. Although faster and more sensitive than viral culture, an additional test is required to determine whether the infection is due to HSV-1 or HSV-2.

Serological assays, blood tests that detect antibodies to HSV, have also been attempted. These tests can detect both symptomatic and asymptomatic infection. However, the tests do not render accurate diagnosis of an acute primary infection until antibodies have formed, usually about two weeks post-infection. Thus, these methods are not useful for diagnosing a first outbreak. Furthermore, the tests often confuse HSV-1 and HSV-2.

Ashley et al., *J. Clin. Microbiol.* (1988) 26:662-667, describe a Western blot test which was stated to detect HSV-2 antibody in 99% of patients with culture-proven HSV-2 infection 21 days after onset of the first symptoms. The test was shown to have 100% accuracy in distinguishing between HSV-1 and HSV-2. However, the test is difficult to perform, utilizing a two-step process to detect antibodies to as many as 50 individual HSV proteins, some of which are specific to type 1 and others to type 2. In addition, two Western blots must be performed (one with HSV-1 antigens and the other with HSV-2 antigens) to determine type specific antibody. The technique is time consuming and interpretation of the results is subjective. Laboratory technicians must undergo extensive training in order to conduct the test properly.

Protein-specific immunoassays have also been developed. See, e.g., Ashley et al., *J. Clin. Microbiol.* (1988) 26:662–667; Sanchez-Martinez et al., *J. Infect. Dis.* (1991) 164:1196–1199; Lee et al., *J. Clin. Microbiol.* (1985) 22:641–644; Lee et al., *J. Virol. Meth.* (1986) 14:111–118. These assays detect antibodies to a single viral protein, such as gG, which is unique to HSV-1 (gG1) and HSV-2 (gG2). The tests can be performed in immunodot format, generally render accurate results in identifying antibodies to HSV-2, but produce large numbers of false positives in identifying HSV-1 antibodies. Furthermore, antibodies to gG2 may not develop for 6–8 weeks after infection and, in 5–10% of subjects, gG antibody remains undetectable using the described assay formats.

The wide spread availability of a type-specific serological assay would be an important tool for the diagnosis of herpes infection in order to stop the epidemic spread of disease.

SUMMARY OF THE INVENTION

The present invention provides a simple, extremely accurate and efficient method for diagnosing HSV infection, as well as for distinguishing between the presence of HSV-1 and HSV-2 infection. The assay method utilizes both type-specific and type-common HSV antigens and can in one embodiment be used in a single-step assay format.

Accordingly, in one embodiment, the subject invention is directed to a method of detecting HSV infection comprising:

(a) providing a biological sample;

(b) reacting the biological sample with one or more purified HSV type-specific antigens and one or more purified HSV type-common antigens under conditions which allow HSV antibodies, when present in the biological sample, to bind to the type-specific antigen and/or said type-common antigen;

(c) providing one or more moieties capable of associating with an immunoglobulin molecule; and (d) detecting the presence or absence of the one or more moieties.

In yet another embodiment, the invention is directed to a method for distinguishing between HSV-1 and HSV-2 infection in a biological sample, the method comprising:

(a) immobilizing a type-specific HSV-1 glycoprotein, e.g., a type-specific gG1 polypeptide and/or a type-specific epitope of gB1, a type-specific HSV-2glycoprotein, e.g., a gG2 polypeptide and a type-common HSV polypeptide, on a nitrocellulose strip;

(b) contacting the nitrocellulose strip from step (a) with the biological sample under conditions which allow anti-HSV-1 and anti-HSV-2 antibodies, when present in the biological sample, to bind to the type-specific HSV-1 or HSV-2 glycoproteins and/or the type-common HSV polypeptide;

(c) providing a detectably labeled anti-human immunoglobulin antibody; and (d) detecting the presence or absence of bound anti-human immunoglobulin antibodies in the biological sample, thereby detecting the presence or absence of HSV-1 and/or HSV-2 infection in the biological sample.

In particularly preferred embodiments, the biological sample is a human serum sample and the HSV polypeptides have all or a part of a transmembrane domain deleted therefrom.

In yet further embodiments, the invention is directed to immunodiagnostic test kits for detecting HSV infection. The kits comprise type-specific and type-common HSV antigens and instructions for conducting the immunodiagnostic test.

In still further embodiments, the invention is directed to an immunodiagnostic test kit for distinguishing between HSV-1 and HSV-2 infection in a biological sample. The test kit comprises a type-specific HSV-1 glycoprotein, e.g., a gG1 polypeptide and/or a type-specific gB1 epitope, a type-specific HSV-2 glycoprotein, e.g., a gG2 polypeptide and a type-common HSV polypeptide immobilized on a nitrocellulose strip, and instructions for conducting the immunodiagnostic test.

These and other embodiments of the present invention will readily occur to those of ordinary skill in the art in view of the disclosure herein.

BRIEF DESCRIPTION OF THE FIGURES

FIG. 1 depicts representative results from a strip immunoblot assay (SIA) according to the present invention.

FIG. 2A shows the precursor gG1 molecule from which the gG1 antigens were derived. FIG. 2B shows the structure of HSV1gG1. FIG. 2C shows the structure of SOD/HSV1gG1M-D. FIG. 2D shows the structure of SOD/HSV1gGIP-D.

FIGS. 3A–3H depict various gG2 antigens. FIG. 3A shows the precursor gG2 molecule from which the gG2 antigens were derived. FIG. 3B shows the structure of HSV2gG2M-D. FIG. 3C shows the structure of SOD/HSV2gG2M-D. FIG. 3D shows the structure of SOD/HSV2gG2R-D. FIG. 3E shows the structure of SOD/HSV2gG2-Nterm. FIG. 3F shows the structure of SOD/HSV2gG2-Cterm. FIG. 3G shows the structure of SOD/gG2M393–D649. FIG. 3H shows the structure of SOD/gG2A489–D649.

FIG. 4 (SEQ ID No; 1) depicts the amino acid sequence of a gB1 type-specific peptide for use in the present assay methods.

DETAILED DESCRIPTION OF THE INVENTION

Figure 2A:
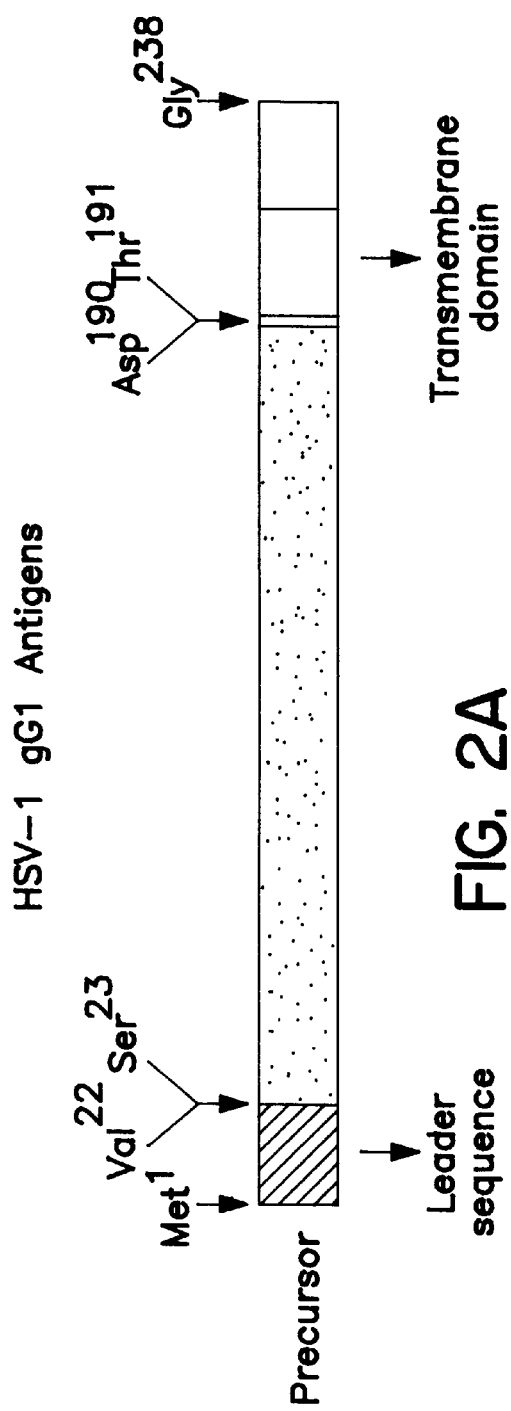
FIGS. 2A–2D depict various gG1 antigens.
Figure 2B:
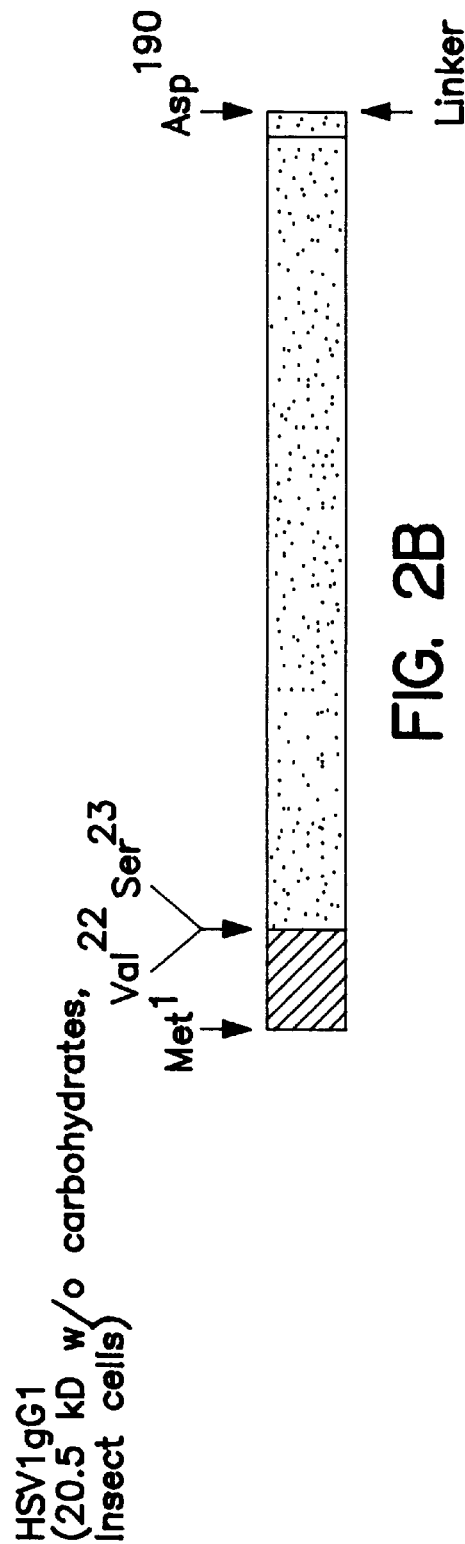

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al., *Molecular Cloning: A Laboratory Manual* (2nd Edition, 1989); *DNA Cloning: A Practical Approach,* vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984); *Fundamental Virology,* 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Furthermore, the amino acid sequences of the various HSV polypeptides described herein are numbered with reference to the full-length precursor molecule, including the signal sequence, unless otherwise specified.

I. Definitions

In describing the present invention, the following terms will be employed, and are intended to be defined as indicated below.

By a "type-specific HSV antigen" is meant a polypeptide derived from either of HSV-1 or HSV-2 which contains one or more epitopes that reacts predominantly with antibodies against either of HSV-1 or HSV-2, but not both HSV-1 and HSV-2. Representative type-specific HSV antigens include HSV-1 and HSV-2 glycoprotein C polypeptides ("gC1" and "gC2") and type-specific peptide epitopes thereof; HSV-1 and HSV-2 glycoprotein G polypeptides ("gG1" and "gG2"), and type-specific peptide epitopes thereof, such as amino acids 111–116 of gG1 and amino acids 357–364, 553–572, 573–580 and 601–608, of gG2 type-specific peptide epitopes of HSV-1 and HSV-2 glycoprotein B ("gB1" and "gB2"), such as amino acids 18-228of gB2 (see, Goade et al., *Abstracts of the 34th Interscience Conference on Antimicrobial Agents and Chemotherapy,* Oct. 4–7 1994, Abstract H6) and type-specific epitopes found within amino acids 1–50 of gB1, numbered with reference to the mature molecule (amino acids 31–80, numbered with reference to the precursor), such as amino acids 1–46 and 1–47 of gB1, numbered with reference to the mature molecule (amino acids 31–76 and 31–77, respectively, numbered with reference to the precursor molecule) (see, Pereira et al., *Virology* (1989) 172:11–24; and the examples below); and type-specific peptide epitopes of HSV-1 and HSV-2 glycoprotein D ("gD1" and "gD2").

By a "type-common HSV antigen" is meant a polypeptide derived from either of HSV-1 or HSV-2 which contains one or more epitopes that reacts with antibodies generated against both of HSV-1 or HSV-2. Representative type-common HSV antigens include gB1, gB2, gD1, gD2, viral protein 16 ("VP16") polypeptides and type-common epitopes thereof, such as those found within amino acids 228–903 of gB2 (see, Goade et al., *Abstracts of the 34th Interscience Conference on Antimicrobial Agents and Chemotherapy,* Oct. 4–7 1994, Abstract H6).

The term "polypeptide" when used with reference to gB, gD, gG, VP16, etc., refers to a gB, gD, gG, VP16, etc., polypeptide, whether native, recombinant or synthetic, derived from any of the various HSV-1 or HSV-2 strains. Thus, the term includes polypeptides from any of the various HSV proteins, including glycoproteins, tegument proteins etc. By "glycoprotein" is meant a polypeptide, whether native, recombinant or synthetic, derived from one found in the HSV membrane, such as gB, gD, gG, etc. The following discussion with reference to polypeptides also applies equally to glycoproteins.

The polypeptide need not include the full-length amino acid sequence of the reference molecule but can include only so much of the molecule as necessary in order for the polypeptide to function for its intended purpose. Thus, if the polypeptide is used as a "type-specific" antigen, only one or more type-specific epitopes of the molecule need be present. If the polypeptide is used as a "type-common" antigen, one or more epitopes of the reference molecule will be present which reacts with antibodies against both HSV-1 and HSV-2.

Thus, the polypeptide may comprise the full-length sequence, fragments, truncated and partial sequences, as well as analogs and precursor forms of the reference molecule. The term therefore intends deletions, additions and substitutions to the sequence, so long as the polypeptide functions as intended. In this regard, particularly preferred substitutions will generally be conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. Proteins having substantially the same amino acid sequence as the reference molecule, but possessing minor amino acid substitutions that do not substantially affect the antibody binding capabilities of the protein, are therefore within the definition of the reference polypeptide.

Particularly preferred deletions of the reference polypeptides include the deletion of all or part of the transmembrane domain and cytoplasmic domain present in the reference molecule. Such deletions allow for enhanced secretion and hence increased recovery of the molecules when produced recombinantly, while still maintaining reactivity with antibodies to HSV-1 and/or HSV-2. The location of a transmembrane domain in a given protein can be determined using a computer program that formulates a hydropathy scale from the amino acid sequence of the protein, utilizing the hydrophobic and hydrophilic properties of each of the 20 amino acids, as described in, e.g., Kyte et al., *J. Mol. Biol.* (1982) 157:105–132; and Hopp and Woods, *Proc. Natl. Acad. Sci. USA* (1981) 78:3824–3828.

By "gB polypeptide" is meant a polypeptide as defined above which is derived from gB1 or gB2. The DNA and corresponding amino acid sequences for gB1 and gB2 are known and reported in, e.g., U.S. Pat. No. 5,244,792; and Stuve et al., *J. Virol.* (1987) 61:326–335. The full-length, precursor gB1protein includes about 904 amino acids of which about 1 to 30 comprise the first hydrophobic region which includes the signal sequence; 31 to about 726 comprise a region of variable polarity; amino acids 727 to about 795 comprise the second hydrophobic region which includes the transmembrane anchor; and amino acids 796 to about 904 constitute the second variable polarity region which includes the cytoplasmic domain. Similarly, the full-length gB2 protein is about 904 amino acids in length. The first 22 amino acids constitute a signal sequence and the mature, non-glycosylated protein, after cleavage of this sequence, has a predicted molecular weight of about 98 kD. Amino acids 23 to about 723 constitute the first region of variable polarity; amino acids 724 to about 798 comprise the transmembrane domain; and amino acids 799 to about 904 constitute the second variable polarity region which includes the cytoplasmic domain.

Representative truncated derivatives of gB, lacking all or a portion of the transmembrane domain and cytoplasmic domain, are described in the examples below, as well as in U.S. Pat. No. 5,244,792 (see, e.g., the description of plasmid pHS114 (ATCC Accession No. 39651), which contains a gB1 gene lacking 580 bp from the 3'-end of the gene and encoding a protein lacking the 194-carboxyl terminal amino acids; and plasmid pHS210 which includes a gB2 gene lacking 637 bp from the 3'-end). U.S. Pat. No. 5,171,568 describes plasmid pHS127A (ATCC Accession No. 39652), having a 1187 base pair gB1 gene fragment. Any of these derivatives, as well as others, which are reactive with HSV antibodies, will find use with the present methods.

By "gD polypeptide" is meant a polypeptide as defined above which is derived from gD1 or gD2. The DNA and corresponding amino acid sequences for gD1 and gD2 are known. See, e.g., U.S. Pat. No. 4,818,694; Lasky and Dowbenko, *DNA* (1984) 3:23–29. The gD1 and gD2 proteins share about 86% homology overall. Full-length gD1 and gD2 both include about 393 amino acids with transmembrane domains at residues 333–362 and cytoplasmic domains extending to the carboxy-terminus at residue 393 The gD1 and gD2 proteins have signal sequences occurring at positions 1 through 25.

Representative truncated derivatives of gD, lacking all or a portion of the transmembrane and cytoplasmic domains, have been described in U.S. Pat. No. 5,171,568 (see, e.g., the description of plasmids pHS211 and pHS213, including gD2 genes encoding the first 305 amino acids and the first 352 amino acids, respectively, of gD2; and the description of plasmid pH132, including a gD1 gene encoding 315 amino acids of gD1); Lasky et al., *Bio/Technology* (June 1984) :527–532 (describing a truncated gD1 gene which encodes for a gD1 polypeptide having the first 300 amino acid residues). Various gD polypeptides have also been constructed which lack all or part of the signal sequence as described in U.S. Pat. No. 4,618,578 (see, e.g., the description of plasmids pYHS116 and pYHS117, which include a 600 bp 5' deletion that includes deletion of the signal sequence coding region of gD1; plasmid pYHS118, which includes the 600 bp deletion above, as well as a 1300 bp deletion in the 3'-end of the coding region which includes most of the anchor sequence of gD1; plasmid pYHS119 which includes the 600 bp deletion to the 5'-end and a 2400 bp deletion in the 3'-end which includes deletion of the entire membrane anchor region and about 700 bp upstream of the anchor sequence of gD1). Any of these derivatives, as well as others, which are reactive with HSV antibodies, will find use with the present methods.

By "gG polypeptide" is meant a polypeptide as defined above which is derived from gG1 or gG2. The DNA and corresponding amino acid sequences for gG1 and gG2 are known. See, e.g., McGeoch et al., *J. Mol. Biol.* (1985) 181:1–13; McGeoch et al., *J. Gen. Virol.* (1987) 68:19–38. The structure of the gG1 gene is shown in FIG. 2A. The gG1 gene encodes a glycoprotein having 238 amino acids, with a predicted signal sequence of 21 amino acids, a first variable polarity region (also called an extracellular domain) of 167 amino acids with 3 potential N-linked glycosylation sites and no cysteine residues, a 24 amino acid hydrophobic transmembrane domain and a C-terminal cytoplasmic domain of 24 amino acids. This protein shares very limited homology with the gG2 protein.

Figure 3A:
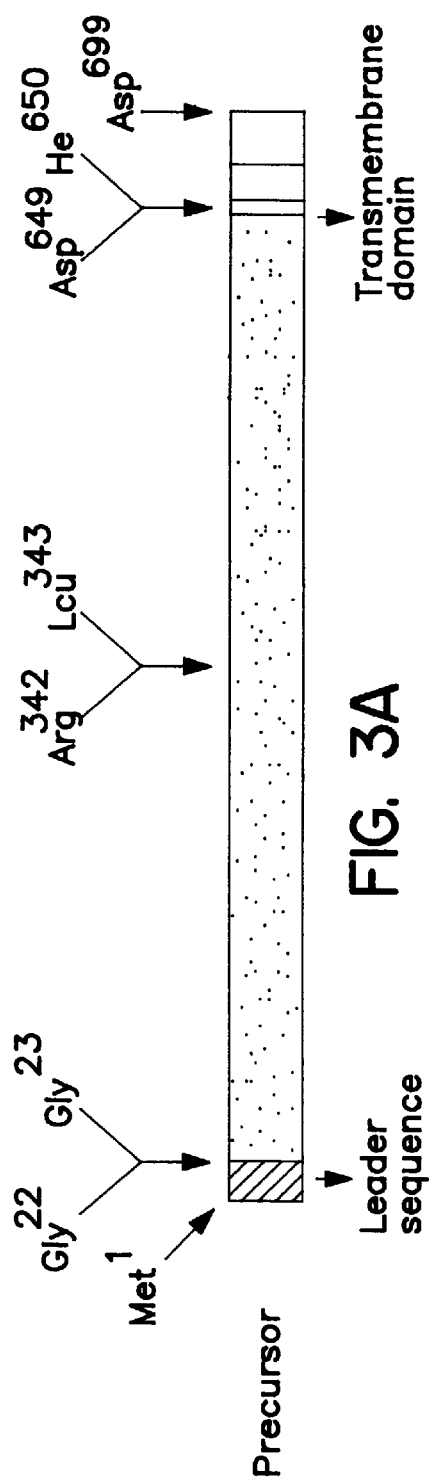
Figure 3B:
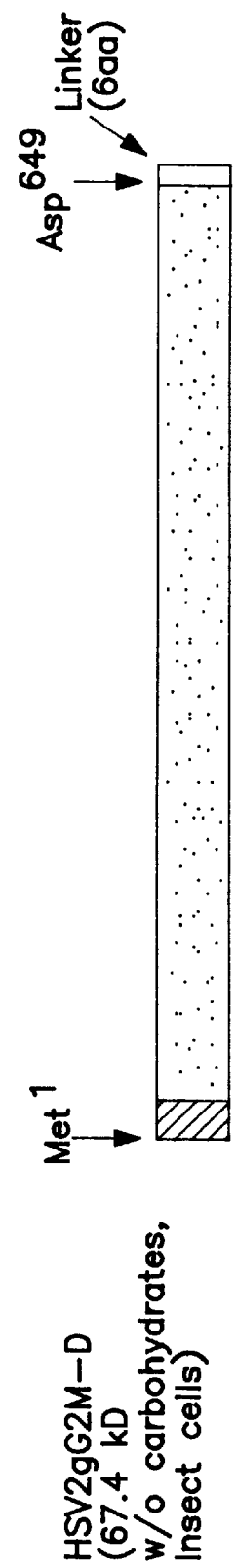
Figure 3C:
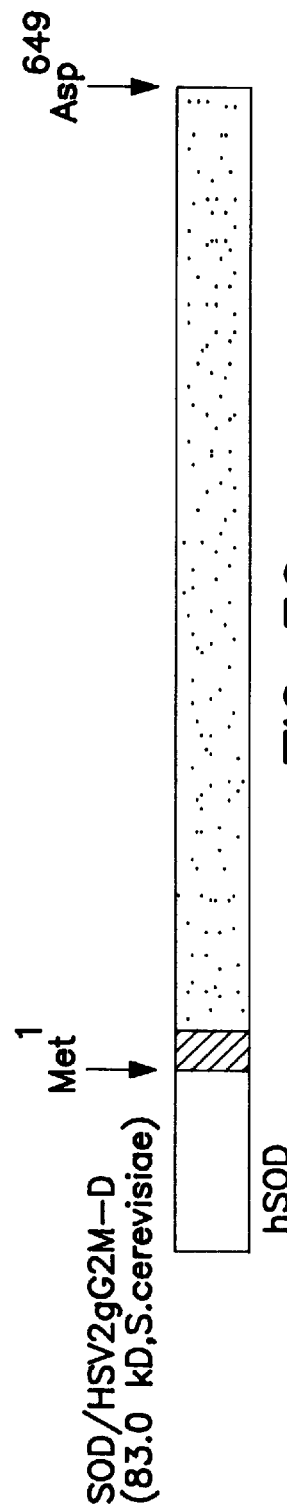
Figure 3D:
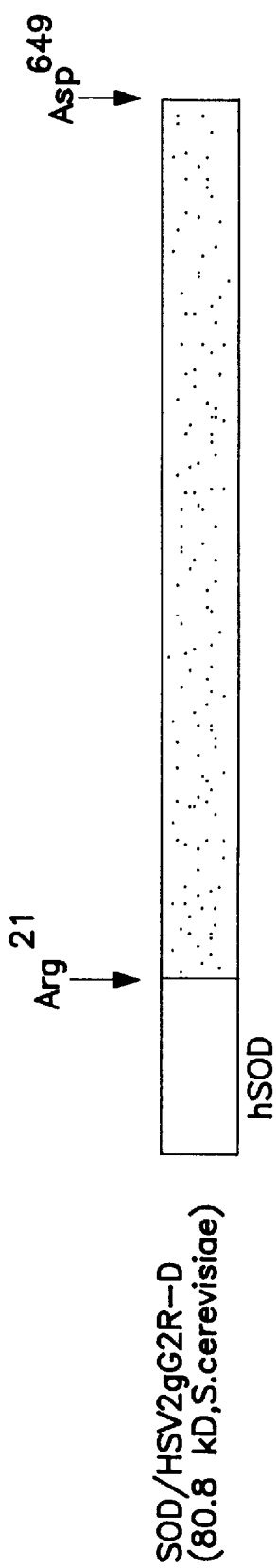
Figure 3E:
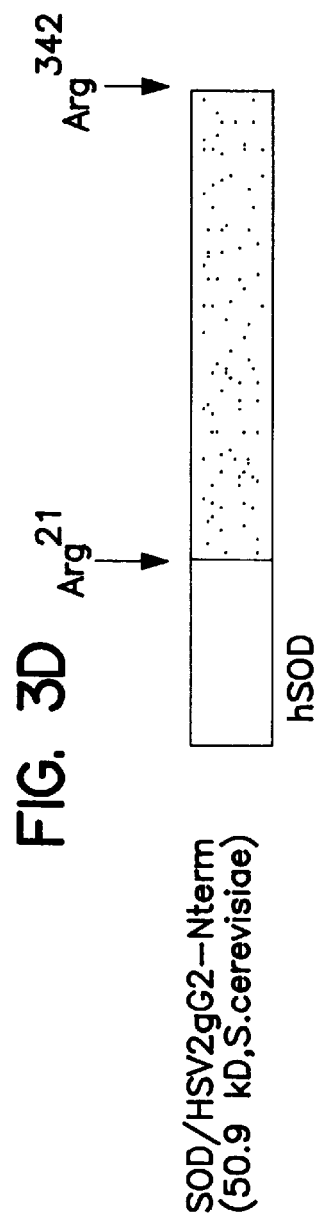
Figure 3F:
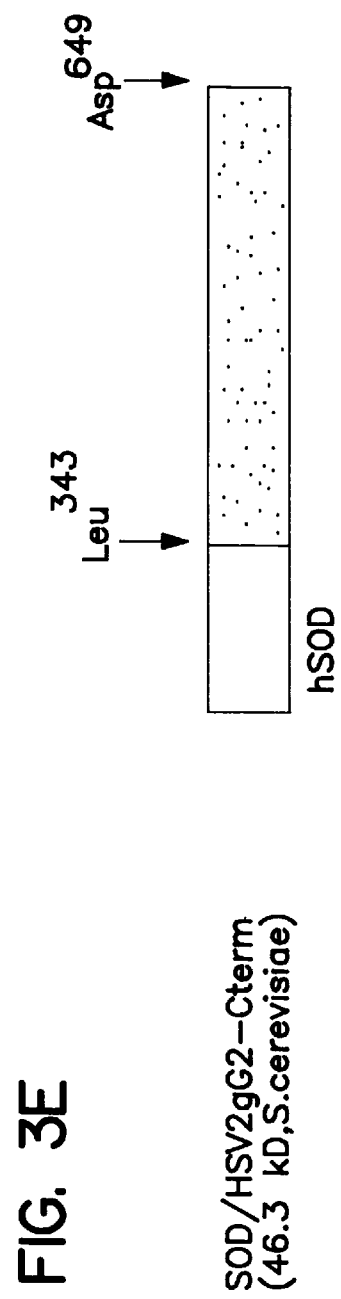

The structure of the gG2 gene is shown in FIG. 3A. The gG2 glycoprotein includes 699 amino acids, has a 21 amino acid signal sequence, a first variable polarity region of 626 amino acids with 4 potential N-linked glycosylation sites and 6 cysteine residues, a transmembrane binding domain of 25 amino acids and a C-terminal cytoplasmic domain of 24 amino acids. The location of three small regions of limited homology between gG1 and gG2, which may serve as useful type-common epitopes, are as follows:

```
        82          91              80% Homology
HSV-1   EEEEGAGDGE                  (SEQ ID NO: 2)

HSV-2   EEFEGAGDGL                  (SEQ ID NO: 3)
        562         571

136                 156     62% Homology
HSV-1   PARPETSRPKTPPTSIIGPLA       (SEQ ID NO: 4)

HSV-2   PARPGAIRPTLPPG ILGPLA       (SEQ ID NO: 5)
        594                 613

171              189        89% Homology
HSV-1   PTPQHTPLFSFLTASPALD         (SEQ ID NO: 6)

HSV-2   PTPQHIPLFWFLTASPALD         (SEQ ID NO: 7)
        632              650
```

A number of truncated derivatives of both of the gG1 and gG2 genes, lacking portions of the C-terminus including the transmembrane binding domain, as well as N-terminally truncated proteins, are described herein (see FIGS. 2, 3 and 4). These derivatives will find use in the subject methods.

By "VP16 polypeptide" is meant a polypeptide as defined above, which is derived from HSV-1 or HSV-2 VP16. VP16 is a viral tegument protein, located between the capsid and the envelope of the virus, and is also known as ICP25, VmW65 and the α-trans-inducing factor (αTIF). The DNA and amino acid sequences of HSV-1 VP16 have been reported. See, e.g., Campbell et al., *J. Mol. Biol.* (1984) 180:1; and Triezenberg et al., *Genes and Develop.* (1988) 2:718. Similarly, the DNA and corresponding amino acid sequences of HSV-2 VP16 are known. See, e.g., International Publication No. WO 92/02251, published Feb. 20, 1992. HSV-1 and HSV-2 VP16 include 489 amino acids. The two proteins share approximately 85% homology. A truncated derivative of VP16, including amino acids 1–416, is described herein. This, as well as other VP16 polypeptides, which are reactive with HSV antibodies, will find use with the present methods.

By "epitope" is meant a site on an antigen to which specific B cells and T cells respond. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art. See, e.g., Geysen et al., *Proc. Natl. Acad. Sci. USA* (1984) 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709–715 (technique for identifying peptides with high affinity for a given antibody). Antibodies that recognize the same epitope can be identified in a simple immunoassay showing the ability of one antibody to block the binding of another antibody to a target antigen.

A "purified" protein or polypeptide is a protein which is recombinantly or synthetically produced, such that the amount of protein present in a composition is substantially higher than that present in a crude viral preparation. In general, a purified protein would be ≧50% homogeneous and more preferably ≧homogeneous.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and α-β-galactosidase.

II. Modes of Carrying Out the Invention

The present invention is based on the discovery of novel diagnostic methods for accurately detecting HSV infection and for discriminating between HSV-1 and HSV-2 infection. The methods utilize type-specific and type-common HSV antigens, thereby reducing the incidence of false results. The methods can be practiced in a simple one-step assay format which allows for both detection of infection, as well as identification of the type of infection present, in a single assay.

More particularly, the presence of a type-common antigen allows the diagnosis of HSV infection in general. The presence of the type-specific antigen allows determination of the virus type, i.e., whether the infection is caused by HSV-1 and/or HSV-2. Due to the presence of the type-common antigen, positive results will occur even in untypable samples. Hence, the incidence of false negatives is reduced.

The antigens for use in the subject diagnostic techniques can be produced using a variety of techniques. For example, the antigens can be generated using recombinant methods, well known in the art. In this regard, oligonucleotide probes can be devised based on the known sequences of the HSV genome and used to probe genomic or cDNA libraries for HSV genes encoding for the antigens useful in the present invention. The genes can then be further isolated using standard techniques and, if desired, restriction enzymes employed to truncate the gene at desired portions of the full-length sequence.

Similarly, HSV genes can be isolated directly from cells and tissues containing the same, using known techniques, such as phenol extraction and the sequence further manipulated to produce the desired truncations. See, e.g., Sambrook et al., supra, for a description of techniques used to obtain and isolate DNA. Finally, the genes encoding the HSV antigens can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge (1981) *Nature* 292:756; Nambair et al., (1984) *Science* 223:1299; Jay et al., (1984) *J. Biol. Chem.* 259:6311.

Once coding sequences for the desired proteins have been isolated or synthesized, they can be cloned into any suitable vector or replicon for expression in a variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego, Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

Viral systems, such as a vaccinia based infection/transfection system, as described in Tomei et al., *J. Virol.* (1993) 67:4017–4026 and Selby et al., *J. Gen. Virol.* (1993) 74:1103–1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

Depending on the expression system and host selected, the antigens of the present invention are produced by growing host cells transformed by an expression vector under conditions whereby the antigen of interest is expressed. The antigen is then isolated from the host cells and purified. If the expression system provides for secretion of the antigen, the antigen can be purified directly from the media. If the antigen is not secreted, it is isolated from cell lysates. The selection of the appropriate growth conditions and recovery methods are within the skill of the art.

The HSV antigens may also be produced by chemical synthesis such as by solid phase or solution peptide synthesis, using methods known to those skilled in the art. Chemical synthesis of peptides may be preferable if the antigen in question is relatively small. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

The type-specific and type-common HSV antigens are used herein as diagnostics to detect the presence of reactive antibodies of the virus in a biological sample. For example, the presence of antibodies reactive with the HSV antigens can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g, beads or microtiter plates); polyvinylidine fluoride; diazotized paper; nylon membranes; activated beads, magnetically responsive beads, and the like.

Typically, a solid support is first reacted with a solid phase component (e.g., one or more type-specific and one or more type-common antigens) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M.A. *Bioconjugate Chem.* (1992)

3:2–13; Hashida et al., *J. Appl. Biochem.* (1984) 6:56–63; and Anjaneyulu and Staros, *International J. of Peptide and Protein Res.* (1987) 30:117–124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with type-specific antigen or type-common antigen. A biological sample containing or suspected of containing anti-HSV immunoglobulin molecules is then added to the coated wells. In assays wherein it is desired to use one microtiter plate, a selected number of wells can be coated with a first type-specific antigen moiety, a different set of wells coated with a second type-specific antigen moiety and a third set of wells with a type-common antigen moiety. In the alternative, a series of ELISAs can be run in tandem, wherein individual plates are used for each type-specific and type-common antigen moiety. After a period of incubation sufficient to allow antibody binding to the immobilized antigens, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-type-specific or anti-type-common antigen ligands from a biological sample can be readily detected using a secondary binder comprising an antibody directed against the antibody ligands. A number of anti-human immunoglobulin (Ig) molecules are known in the art (e.g., commercially available goat anti-human Ig or rabbit anti-human Ig) which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the viral proteins and antibodies specific for those proteins form complexes under precipitating conditions. In one particular embodiment, type-specific and/or type-common antigen can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for type-specific and/or type-common HSV antigen. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of anti-bodies from a biological sample suspected of containing anti-type-specific and/or anti-type-common molecules is immobilized to a substrate. In this regard, an initial affinity purification of the sample can be carried out using immobilized antigens. The resultant sample preparation will thus only contain anti-HSV moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, type-specific and type-common antigens, each having separate and distinct labels, are contacted with the bound antibodies under suitable binding conditions. After any non-specifically bound antigen has been washed from the immunoaffinity support, the presence of bound antigen can be determined by assaying for each specific label using methods known in the art.

A particularly preferred method for diagnosing HSV infection using the present invention involves the use of strip immunoblot assay (SIA) techniques, such as those known in the art which combine traditional Western and dot blotting techniques, e.g., the RIBA® (Chiron Corp., Emeryville, Calif.) test. In these assays, one or more type-specific and one or more type-common antigens are immobilized as individual, discrete bands on a membranous support test strip. Visualization of anti-HSV reactivity in the biological sample is accomplished using anti-human IgG enzyme-conjugates in conjunction with a calorimetric enzyme substrate. Internal controls, such as anti-human IgM and human IgG, can also be present on the strip. The assay can be performed manually or used in an automated format.

The above-described assay reagents, including the type-specific and type-common antigens, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Production of Recombinant qG1 Polypeptides for use in HSV Diagnostic Assays a. SOD/HSV1qG1M-D.

Two oligonucleotides, 5'AGG AAC CAT GGC AAT GTC GCC GGG CGC CAT GCT GGC CGT TGT T3' (SEQ ID NO:8) and 5'TCC CGT CGA CTA CTA GTC CAG GGC GGG GGA GGC AGT GAG GAA CGA3'(SEQ ID NO:9), were used to prime the PCR synthesis of a DNA fragment encoding for an amino terminal region of 190 amino acids ($Met_1$-$Asp_{190}$) of gG1 of HSV-1, strain Patton (Kudler et al., Virology (1983) 124:86–99). (See FIG. 2B) This polypeptide corresponds to $Met_1$-$Asp_{189}$ of the gG1 glycoprotein previously reported by McGeoch et al. for HSV-1, strain 17 (McGeoch et al., J. Mol. Biol. (1985) 181:1–13). The one amino acid discrepancy is due to the fact that the DNA used as template in the PCR experiments (plasmid pSVgG1) was derived from a HSV-1 isolate that encodes for one additional glutamic acid in the corresponding gG1 $Glu_{79}$-$Glu_{85}$ amino acid stretch of HSV-1, strain 17.

The PCR-synthesized DNA fragment contained an NcoI restriction site and an ATG codon at the 5'-end, and two stop codons and the restriction site SalI at the 3' end. These modifications were introduced to facilitate the cloning of the viral protein. DNA was digested with NcoI/SalI and the 583 bp fragment was cloned into a bacterial vector derived from pSOD/HIV2PR113 (Pichuantes et al., J. Biol. Chem. (1990) 265:13890–13898) to generate plasmid pSODgG1. This bacterial expression plasmid encodes for SOD/HSV1gG1M-D, a hybrid protein having a molecular mass of 35.7 kD and consisting of human superoxide dismutase (SOD) and the HSV-1 gG1 amino acid sequence mentioned above (FIG. 2C).

b. SOD/HSV1gG1P-D.

Figure 2C:
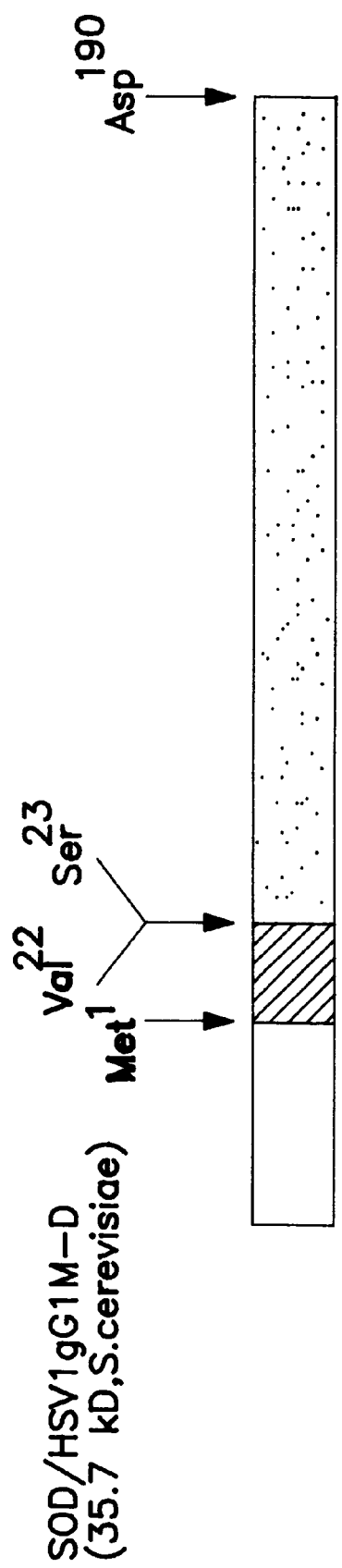
Figure 2D:
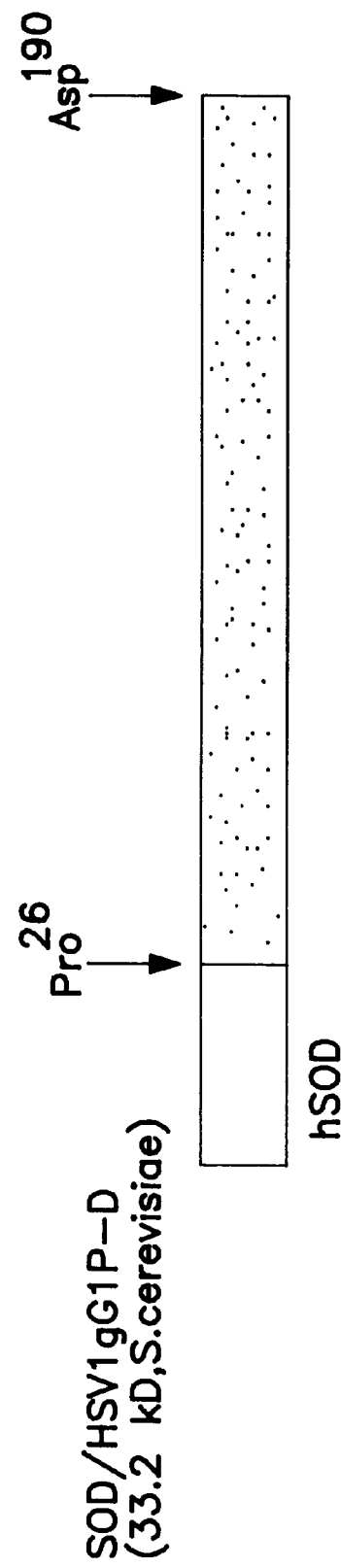

This recombinant antigen of 33.2 kD is similar to the SOD/HSV1gG1M-D antigen described above, except that the signal sequence was not included (FIG. 2D).

```
5' end                    PstI      Met
    5' AGT ACC GGA TCC CTG CAG ATG TCG CAG GGC GCC ATG     (SEQ ID NO: 10)

CGT G

3' end              BamHI     Stop       Glu epitope
    5' TTA TCA GGA TCC CTA TTC CAT TGG CAT GTA TTC GTC     (SEQ ID NO: 11).

CAG GGC GGG GGA GGC AGT
``` c. Expression of gG1 Antigens in Yeast.

For expression of the recombinant proteins described above in yeast, the following manipulations were undertaken: the 833 bp StuI/SalI insert of plasmid pSI1/PR179 encoding for the HIV-1 protease (Pichuantes et al., Proteins Struct. Funct. Genet. (1989) 6:324–337) was replaced by the 918 bp StuI/SalI fragment isolated from pSODgG1 to generate the plasmid shuttle vector pSI/gG1. The 2408 bp BamHI/Sal1 cassette containing the ADH2/GAPDH promoter-SOD/HSV1gG1 sequence was removed from pSI/gG1 and cloned into the yeast vector pBS24.1 (Pichuantes et al. in "Protein Engineering: A Guide to Design and Production," Chapter 6, J. L. Cleland and C. Craik, eds., John Wiley & Sons, New York, N.Y., in press). Resulting plasmid pSODHSV1gG1M-D contains 2μ sequences for autonomous replication in yeast, the hybrid promoter ADH2/GAPDH, the α-factor terminator to ensure transcription termination, and the yeast genes lue2-d and URA3 for selection. The ColE1 origin of replication and the α-lactamase gene required for plasmid replication and selection in bacteria are also present in this recombinant plasmid. A similar procedure was followed for the plasmid encoding SOD/HSV1gG1P-D.

Cells of S. cerevisiae JSC310 [MAT a, leu2, ura3-52, prb1-1122, pep4-3, prc1-407, ::DM15 (pGAP/ADR1::G418$^r$), (cir°)] were transformed with the pSODHSV1gG1M-D plasmid and, after depletion of glucose in the yeast medium (Pichuantes et al., J. Biol. Chem. (1990) 265:13890–13898 and Franzusoff et al., J. Biol. Chem. (1995) 270:3154–3159), expressed a fusion protein of 35.7 kD consisting of SOD (153 amino acids), a linker of 2 amino acids (Met-Ala) and a HSV-1 gG1 polypeptide of 190 amino acids (FIG. 2C). The nucleotide sequence was verified by DNA sequencing of the SOD/HSV1 gG1 coding region of pSOD-HSV1 gG1 M/D.

The recombinant proteins were expressed at high levels in yeast, as detected by Coomassie-blue staining and immunoblot analysis using monoclonal antibodies to SOD and HSV-1 positive sera. The protein was purified as follows. The transformed yeast cells were lysed and the lysate centrifuged at 10,000 rpm for 1 hour. The supernatant was diluted 1:10 in 50 mM MES (2-[N-Morpholino] ethanesulfonic acid), pH 5.2 and run on an S-Sepharose column. Protein was eluted using a 0 to 1M NaCl gradient, the protein peak pooled and concentrated and further purified using Sephacryl S-200 HR gel filtration. The protein peak was pooled, concentrated and stored for further use.

d. gG1t

An additional truncated derivative of gG1, termed gG1t, was made which included amino acids 1 to 189, including the signal sequence and the entire extracellular domain of gG1, as follows. The gene encoding gG1t was cloned from HSV-1 EcoRI fragment H (strain Patton) by PCR using the following primers:

Protein gG1t was expressed using an insect cell system as follows. The PCR fragment was digested with PstI and BamHI, inserted into the pAcC13 baculovirus expression plasmid (Munemitsu et al., Mol. Cell. Biol. (1990) 10:5977–5982) and sequenced in its entirety using the dideoxy chain termination method. This fragment contained 567 nucleotide base pairs 5' to the translational start and the region encoding amino acids 1 to 189, including the signal sequence and the entire extracellular domain. At the 3'-end of the fragment, the primer also encoded a 6-amino acid glu epitope tag (5'TTC CAT TGG CAT GTA TTC 3')(SEQ ID NO:12). This tag facilitates the identification, quantification and purification of any protein bearing it by the use of a corresponding antibody that specifically recognizes the glu epitope.

The DNA sequence encoding gG1t was recombined into Autographa californica baculovirus (AcNPV) via the pAcC13 transfer vector (Munemitsu et al., Mol. Cell. Biol. (1990) 10:5977–5982) by co-transfecting 2 μg of the transfer vector pAc-gG1t or pAc-gG2t DNA with 0.5 μg of linearized, wild-type viral DNA into SF9 cells as described (Kitts et al., Nuc. Acids Res. (1990) 18:56675672.) Recombinant baculoviruses were isolated by plaque purification (Smith et al., Mol. Cell. Biol. (1983) 3:2156–2165). Supernatants from suspension cultures of $1.5 \times 10^6$ recombinant AcNPV-infected SF9 cells per ml were harvested following 48 hours of infection in 1L glass erlenmeyer flasks, shaking at 120 rpm with the relevant baculovirus at an moi of 2–10, in serum-free medium (Maiorella et al., Biotech. (1988) 6:1406–1410). The medium was centrifuged for 10 minutes, 400–600×g at 4° C., 0.8 μm filtered, concentrated and stored at −80° C. prior to purification.

The gG1 polypeptide was immunopurified by adding the non-ionic detergent NP-40 to the thawed concentrated supernatant to a final concentration of 0.2%. The supernatant was incubated at room temperature for 15 minutes, centrifuged at 9000 rpm for 10 minutes, and applied to an affinity column prepared by coupling anti-glu monoclonal antibody to protein G-Sepharose Fast Flow (Pharmacia). The bound protein was eluted with gly-peptide in phosphate buffered saline (PBS) and concentrated.

Purified protein was assessed using SDS-PAGE. The mobility of the gG1t band corresponded to that of a protein of molecular mass 35 kD. The purified protein was digested with N-glycanase to remove all N-linked carbohydrate chains. The protein was subjected to amino acid analysis. The predicted amino acid composition of gG1t agreed very well with that measured. N-terminal amino acid sequencing was performed on the protein using Edman degradation. The gG1t protein began at $Val_{22}$, as predicted by the sequence analysis, affirming that the protein has a 21 amino acid signal sequence.

The identity of the protein was also confirmed by Western blot analysis. A single band with mobility corresponding to that of the Coomassie-blue stained protein was reactive with an anti-glu monoclonal antibody and an alkaline phosphatase conjugated goat anti-mouse IgG.

EXAMPLE 2

Production of Recombinant gG2 Polypetides for use in HSV Diagnostic Assays a. gG2t.

A truncated derivative of the gene encoding gG2 (gG2t) was cloned from HSV-2 HindIII fragment L (strain 333) by PCR using the following primers:

```
5' end                       PstI    Met
    5' AGT ACC GGA TCC CTG CAG ATG CAC GCC ATC GCT    (SEQ ID NO: 13)

CCC AGG

3' end              BamHI    Stop         Glu epitope
    5' TTA TCA GGA TCC CTA TTC CAT TGG CAT GTA TTC ATC    (SEQ ID NO: 14)

TAG AGC AGG GGA GGC CG
```

The PCR fragment was digested with PstI and BamHI, inserted into the pAcC13 baculovirus expression plasmid and sequenced in its entirety using the dideoxy chain termination method. This fragment contained 1953 nucleotide base pairs 5' to the translational start and the region encoding amino acids 1 to 651 including the signal sequence and the entire extracellular domain. At the 3'-end of the fragment, the primer also encoded the 6-amino acid gly epitope tag (5'TTC CAT TGG CAT GTA TTC(SEQ ID NO:12) 3'), described above.

The DNA sequence encoding gG2t was recombined into *Autographa californica* baculovirus (AcNPV) via the pAcC13 transfer vector (Munemitsu et al., Mol. Cell. Biol. (1990) 10:5977–5982), as described with respect to gG1t above.

The purified protein was assessed using SDS-PAGE. The mobility of the gG2t band corresponded to that of a protein of molecular mass of 90 kD. The purified protein was digested with N-glycanase to remove all N-linked carbohydrate chains. The protein was subjected to amino acid analysis. The gG2t composition did not match that calculated from the sequence.

To determine the source of the discordance, N-terminal amino acid sequencing was performed using Edman degradation. The gG2t protein began with the sequence Ala-Leu-Thr corresponding to amino acid $Ala_{345}$ in the middle of the extracellular domain. Thus, the gG2 protein expressed in baculovirus-infected insect cells is cleaved as has previously been described for the viral gG2 protein and gG2 protein expressed in the absence of other viral proteins in mammalian cells. The protein appears to be cleaved between $Met_{344}$ and $Ala_{345}$.

The identity of the gG2t protein was confirmed by Western blot analysis. A single band with mobility corresponding to that of the Coomassie-blue stained protein was reactive with an anti-gG2 monoclonal antibody and a horseradish-peroxidase conjugated anti-mouse antibody.

b. SODIHSV2gG2Arg21-Arg342 (N-terminal Region) and SOD/HSV2qG2Leu343-Asp649 (C-terminal Region).

Since, as explained above, it was discovered that recombinantly produced gG2 protein is cleaved intracellularly by a protease between amino acids 344 and 345, gG2 proteins were produced as two fragments, consisting of SOD fusions to Gly22-Arg342 and Leu343-Asp649, respectively, in order to achieve high levels of expression.

Two constructs were made to express the amino terminal portion (FIG. 3E) and the carboxyl terminal portion (FIG. 3F) of the molecule. The N- and C-terminal gG2 constructs were expressed in insect cells as follows. The strategy for subcloning sequences encoding the C-terminus of gG2 from HSV-2 involved generation of a 174 bp PCR product for cloning between unique PstI and NcoI sites of the plasmid, pAcgG2L, a baculovirus transfer vector for full-length gG2. The 5-prime amplimer, 5'd-AACTGCAGAAATGCTGG GGCCCTGCATGCTGCTGCTGCTGCTG CTGCTGGGCCTGAGGCTACAGCTCTC-CCTGGGCATCGCCTTGACCGAGGACGCGTCC TCCGAT-3' (SEQ ID NO:15), was designed to contain a PstI restriction site complementary to the cloning site in the vector pAcgG2L, followed by a consensus eukaryotic start site and the 21 codons of the human placental alkaline phosphatase signal sequence with an Ile at amino acid position 1 for correct cleavage of the peptide, followed by 9 codons of the C-terminus of gG2 ($Ala_{345}$-$Asp_{354}$). The downstream amplimer, 5'd-AGGGCGCCATGGCGGTGGCCGACA-3' (SEQ ID NO:16), was synthesized to contain an NcoI recognition site adjacent to the four codon gG2 sequence directly upstream. The NcoI site facilitates the insertion of the PCR product in place of the 1.1 kb sequence encoding N-terminal gG2 removed during digestion and purification of the vector, pAcgG2L with PstI and NcoI. Standard PCR reactions were performed with vent polymerase (New England Biolabs, Beverly, Mass.) according to the manufacturer's recommendations. Amplified products were gel purified using Geneclean (RPI, Mount Prospect, Ill.) and exhaustively digested with PstI and NcoI and ligated into PstI/NcoI-cut pACgG2L. The origin and fidelity of the PCR product cloned into the vector was verified by the forward sequencing primer 5'D-GATAACCATCTCGCAAATAAATAAG-3' (SEQ ID NO:17) and the reverse sequencing primer 5'd-CATCTCGTCGGGGGGAGTAGT-3' (SEQ ID NO:18) which flank the unique PstI and NcoI cloning sites, respectively, in the baculovirus transfer vector. The modified transfer vector containing the alkaline phosphatase leader sequence and N-terminally truncated gG2, was designated pAcapgG2L.

The sequence encoding the C-terminus of gG2 was recombined into the *Autographa californica* baculovirus (ACMNPV) via the transfer vector pAcapgG2L, (parent vector pAcC13, Munemitsu et al., Mol. Cell. Biol. (1990) 10:5977–5982) by co-transfecting Sf9 insect cells with 2 μg of plasmid DNA with 0.5 μg linearized, wild-type viral DNA as described (Kitts et al., *Nuc. Acids Res.* (1990) 18:5667–5672). Recombinant baculovirus was isolated by plaque purification (Smith et al., *Mol. Cell. Biol.* (1983) 3:2156-2165). Log-phase, suspension cultures of 1.5×10e6 Sf9 cells per ml were infected with baculovirus, at an moi of 2–10, for production of recombinant protein in ISFM7 media (Maiorella et al., *Biotech.* (1988) 6:1406–1410). Serum-free supernatants were harvested for protein purification approximately 48 hours post infection.

The N- and C-terminal gG2 proteins were also expressed in yeast strains AB122, JSC310 and AD1. High expression level of SOD/HSV2gG2Arg$_{21}$-Arg$_{342}$ protein was detected by Coomassie-blue staining in the yeast insoluble fractions.

```
5' end      BglII      Met   VP16
   5' ACA GAT CTT ATG GAC CTG TTG GTC GAC        (SEQ ID NO: 19)

3' end      EcoRI    Stop   Glu epitope
   5' AG AAT TCA CTA TTC CAT TGG CAT

VP16
GTA TTC GGT GGA CAG TCT GCG                       (SEQ ID NO: 20)
```

The protein has an apparent molecular weight of ~55 kD (translated molecular weight is 50.9). Expression in yeast strains AB122 and JSC310 was higher than in strain AD1. The protein immuno reacted with anti-HSV-2 antibodies.

SOD/HSV2gG2Leu$_{343}$-Asp$_{649}$ was not detected in the insoluble fractions of AB122, JSC310 or AD1. Further experiments (Coomassie-blue staining and immunoblot analysis) indicated that the protein was found in the soluble fraction of AB122 and JSC310 cells. The protein had an apparent molecular weight of ~80 kD (translated molecular weight is 46.3 kD).

Yeast expression of SOD/HSV2gG2-Nterm and SOD/HSV2gG2-Cterm, as detected in total lysates of cells coming from 5 independent colonies (C1 to C5), were as follows. Coomassie-blue stained proteins showed that the N-terminal antigen (predicted molecular weight=50.9) was expressed at high levels in all cultures (C1 to C5). This protein reacted with MAbs to hSOD and exhibited a weak reactivity with antibodies present in an HSV-2 positive serum. The C-terminal antigen (predicted molecular weight=46.3) was not detected by Coomassie-blue staining. A protein band with an apparent molecular weight of ~80 kD was detected in the Western blots. This protein strongly reacted with the HSV-2 positive sera.

In order to better characterize the recombinant proteins expressed in the cells, total, soluble and insoluble fractions of each C3 clone were prepared. Results indicated that the N-terminal antigen was mostly found in the insoluble fraction (as expected for a hSOD/env protein). The C-terminal antigen was not detected by Coomassie-blue staining but was clearly identified by its reactivity to MAbs to hSOD and to the HSV-2 positive sera. Surprisingly, for a hSOD/env protein, the antigen was detected in both soluble and insoluble fractions (more reactivity in the soluble fraction). A protein band of ~30 kD was also detected in the immunoblots.

c. SOD/Gq2M393-D649

A PCR DNA product encoding for a smaller HSV2gG2C-terminal polypeptide was constructed that consisted of an SOD fusions to Met$_{393}$-Asp$_{649}$ of gG2. (see FIG. 3G).

d. SOD/qG2A489-D649

A PCR DNA product encoding for a smaller HSV2gG2 C-terminal polypeptide was constructed that consisted of an SOD fusions to Ala$_{489}$-Asp$_{649}$ of gG2. (see FIG. 3H).

EXAMPLE 3

Production of truncated HSV VP16 for use in HSV Diagnostic Assays

A truncated HSV VP16 polypeptide was expressed in a baculovirus system as follows. A truncated derivative of HSV-2 strain G VP16, VP16-2t, encoding amino acids 1–416 with the six-amino acid glu-epitope tag at the C-terminus, was cloned by PCR amplification from plasmid pSVVP-2 (described below) using the following primers:

The 1.38 kb PCR fragment was digested with BglII and EcoRI, inserted into the pAcC13 baculovirus expression plasmid (Munemitsu et al., Mol. Cell. Biol. (1990) 10:5977–5982) and sequenced in its entirety using the dideoxy chain termination method. The new plasmid was designated as pAcVP16T.

The DNA sequence encoding VP16-2t was recombined into *Autographa californica* baculovirus (ACNPV) as described with respect to gG1t above.

Plasmid pSVVP-2 was obtained by isolation of the ~2.0 kb EcoRI—BamHI fragment encoding VP16-2 from pHS226 (International Publication No. WO 92/02251; ATCC Accession No. 68372) and insertion into pSV7d that had previously been digested with EcoRI and BamHI.

pHS226 was generated from pUC18 into which was cloned an XhoI—SphI blunt end fragment encoding VP16-2 obtained from pH2G512, cloned into the SmaI site of pUC18.

The truncated VP16 polypeptide was immunopurified as follows. VP16-2t was extracted from the pellet of the baculovirus cell culture with a buffer consisting of 20 mM Tris-HCl, pH 8.2, 1 mM EGTA, 1 mM MgCl$_2$, 4 mM beta-mercaptoethanol, 1 μg/ml aprotinin, 0.2% NP-40, and anti-proteinase cocktail consisting of pepstatin, leupeptin, E-64, pefabloc SC, EDTA and EGTA. The extract was cleared by centrifugation and VP16 was purified on an anti-glu Protein G-Sepharose Fast Flow (Pharmacia) column eluted with glu-peptide in PBS.

The purified protein was characterized by SDS-PAGE. The mobility of the VP16 band corresponded to that of a protein of molecular mass 65 kD for full length VP16 and 45 kD for the truncated form of VP16. The identity of the protein was confirmed by Western blot using antiglu monoclonal antibody and LP1, a monoclonal antibody to the N-terminus of VP16.

EXAMPLE 4

Production of Recombinant gD polypeptide for use in HSV Diagnostic Assays

A gD2 gene fragment, encoding amino acids 1–302 of the extracellular domain, was cloned into the mammalian expression vector pSV7d to generate pHS213 as previously described (U.S. Pat. No. 5,171,568). The plasmid was transfected into CHO Cells and stable cell lines that expressed the truncated gD2 derivative protein were selected and then amplified by serial exposures to increasing concentrations of methotrexate. The truncated protein was purified from media using standard techniques. In particular, conditioned media was concentrated, the concentrated media was acid precipitated, and a series of columns used, including a heparin Sepharose, Butyl 650M and Q-Sepharose fast flow column. The product was concentrated, dialfiltered and stored for further use.

EXAMPLE 5

Production of Recombinant gB Polypeptides for use in HSV Diagnostic Assays a. HSV gB Full-length gB polypeptides, as well as fragments of gB which contain deletions of the transmembrane and cytoplasmic domains, for use in the present diagnostic assays, are recombinantly produced using the methods disclosed in U.S. Pat. Nos. 5,171,568 and 5,244,792; Pachl et al., *J. Virol.* (1987) 61:315–325.

b. Truncated Derivatives of HSV gB

Various truncated derivatives of HSV gB, lacking all or a portion of the transmembrane domain and cytoplasmic domain, were constructed as described in U.S. Pat. Nos. 5,171,568 and 5,244,792. In particular, plasmid pHS114 (ATCC Accession No. 39651) was constructed, which contains a gB1 gene lacking 580 bp from the 3'-end of the gene and encoding a protein lacking the 194-carboxyl terminal amino acids. Plasmid pHS210 was also made which includes a gB2 gene lacking 637 bp from the 3'-end). Plasmid pHS127A (ATCC Accession No. 39652), was also constructed, having a 1187 base pair gB1 gene fragment.

c. HSVgB2dTM

Plasmid pPRgBdTM, an expression vector for a gB2 antigen, contains a deletion derivative of the gB gene under the control of the SV40 early promoter. The gB gene derivative encodes a polypeptide 808 amino acids in length which lacks a region defined by amino acids $Ala_{703}$ to $Leu_{776}$, which includes the transmembrane (TM) region. The construct includes amino acids $Gln_{777}$ through the C-terminus.

This derivative was constructed to improve the secretion efficiency of the gB2 protein compared to truncated gB2 used previously, wherein both the transmembrane domain and the C-terminal region were deleted. Both protein derivatives contain substantially all of the extracellular domain of the gB protein. The gB2 polypeptide encoded by the construct, gB2dTM, has two new amino acids, $Gly_{702}$ and $Thr_{703}$, that were inserted as the result of the cloning and the introduction of a KpnI site at the fusion between the extracellular and cytoplasmic domains.

Plasmid pPRgBdTM also contains the SV40 origin of replication, the SV40 poly A addition site and the dihydrofolate reductase cDNA under the control of the adenovirus major late promoter (Ad-dhfr). The construction of all plasmids is described in detail below.

d. Construction of plasmid pPRgBdTM

The scheme used to construct pPRgBdTM is as follows. The gB2dTM derivative gene sequence was obtained as a 2.57 kp EcoRI-BamHI fragment from plasmid pHS214-A. The fragment was incubated with the Klenow fragment of DNA polymerase I to repair the EcoRI and BamHI sites to blunt ends and then was ligated to the mammalian cell expression vector pPR25 that had previously been cut with SalI and the ends repaired to blunt with Klenow DNA polymerase I fragment followed by treatment with alkaline phosphatase.

The construction of plasmid pHS214-A was as follows. The complete HSV-2 gB sequence is contained within a 3467 bp NruI to BamHI fragment in plasmid pHS208 (described in U.S. Pat. No. 5,171,568). The gB2 derivative gene, gB2dTM lacking amino acids $Asp_{701}$ to $Gln_{776}$ of the transmembrane domain, was assembled from three fragments: (1) The 5'-end of the gB2 gene containing the 22 amino acid signal sequence and 604 amino acids of the extracellular domain, $Ala_1$ through $Ala_{604}$, as well as all of the pSV7d (described in U.S. Pat. No. 5,171,568) vector sequences including the SV40 promoter, the SV90 polyadenylation site and the sequences required for replication in bacteria were obtained as a 4360 bp XhoI to BamHI fragment from plasmid pHS214; (2) The remainder of the extracellular domain of gB2 from $Leu_{605}$ to $Asp_{701}$ was obtained from plasmid pHS208 as a PCR fragment of 294 bp with primer A containing the natural XhoI site complementary to nucleotide 1870 to 1980 (considering the initial ATG of the gB gene as nucleotide 1) and primer B complementary to nucleotides 2158 to 2169 and containing an introduced KpnI site. This fragment was digested with the restriction enzymes XhoI and KpnI and isolated by agarose gel electrophoresis; and (3) The 3' end of the gB2 gene, comprising the cytoplasmic domain containing amino acids $Gln_{776}$ to the stop codon at amino acid position 883 was prepared from plasmid pHS208 as a 321 bp KpnI to BamHI fragment by using PCR primers C complementary to nucleotides 2395 to 2407 containing the engineered KpnI site and PCR primer D complementary to nucleotides 2698 to 2715 containing the stop codon and the BamHI site. This fragment was digested with the restriction enzymes KpnI and BamHI and isolated by gel electrophoresis. These three fragments, 1, 2 and 3, were ligated together to generate plasmid pHS214-A containing the derivative gB2dTM gene in the expression vector pSV7d.

Plasmid pPR25 is a mammalian cell expression vector containing the dihydrofolate reductase (dhfr) cDNA under the control of the adenovirus-2 major late promoter (Ad-2 MLP), SV40 DNA encoding the small T antigen intron and polyadenylation sequences. The construction of pPR25 required the digestion of plasmid pPR21 with StuI and the insertion of a 3388 bp NruI-EcoRI fragment from expression vector, pAD-dhfr. Plasmid pPR21 was derived from pSV7d by inserting a synthetic 85-mer, containing the bla promoter and the restriction sites for StuI and XhoI, into the SspI site in the poly linker.

The scheme used to construct pHS214 is as follows. The truncated derivative of the gB2 gene was obtained as two fragments which were ligated together into the expression vector. The 3'-end of the coding sequence was obtained from pHS208 which was digested with TthIII and a 1660 bp fragment was isolated. The fragment ends were filled-in with Klenow fragment of DNA polymerase I, the DNA was digested with SphI and a 477 by SphI-(TthIII) fragment was isolated containing sequences encoding for gB2 amino acids 560–718.

The 5'-end of the truncated gB2 gene was obtained from pHS210, (described in U.S. Pat. No. 5,244,792) a plasmid which contains a 1.90 kbp HindIII-PvuII fragment encoding 591 amino acids of the gB2 protein. The gB2 coding region in pHS210 is truncated at a PvuII site, 110 amino acids N-terminal to the proposed membrane anchor sequence. pHS210 was digested with HindIII, the fragment ends were filled-in with the Klenow fragment of DNA polymerase I and the DNA was digested with SphI. A 1735 bp (HindIII)-SphI fragment was isolated.

The two gB2 gene fragments isolated above were ligated together, the fragment ends were filled with the Klenow fragment of DNA polymerase I and inserted into pSV7d, previously digested with XgaI and repaired to blunt ends with the Klenow fragment of DNA polymerase I, to generate pHS214.

e. Expression of gB2dTM in mammalian cells

Plasmid pPRgBdTM was transfected into both COS7 cells and dhfr CHO cells. Expression of the gB2 protein into the culture medium was confirmed by an ELISA as described by Stuve et al., *J. Virol.* (1987) 61:326–335. A CHO cell line expressing the secreted gB2dTM was selected for large scale commercial production. For this purpose, CHO cells lacking an endogenous dihydrofolate reductase (gene encoding the dhfr enzyme) were transfected with a DNA plasmid vector containing genes for both dhfr as well as an HSV gB2 derivative, gB2dTM. The transfected cells were grown in selective culture medium such that only cells that expressed dhfr could grow. The level of gB production by these cells was increased by a stepwise process of culture in selective medium containing increasing concentration of the drug methotrexate (MTX), a noncompetitive inhibitor of dhfr. Cells acquired the ability to grow in the presence of MTX by amplifying the number of copies of the dhfr gene, Alt et al., *J. Biol. Chem.* (1978) 235:1357–1370; Kaufman et al., *Mol. Cellular Biol.* (1981) 1:1069–1076. A second gene, gB2, that was directly linked to the dhfr DNA was also co-amplified, Kaufman, R. J., et al., *J. Mol. Biol.* 159:601–621 (1982). This process entailed exposure of cells in a bulk population to selective medium with MTX, selection of 50–400 discrete single colony clones, expansion of the colony cell number by serial passage in 96 well-plates, then 24 well and 6 well plates with concurrent evaluation of gB productivity using an ELISA assay to measure the amount of gB secreted into the culture medium. This process was stopped when no further gains in productivity were observed.

EXAMPLE 6

Identification of gB2 Type-Specific and Type-Common epitopes

Recombinant proteins representing three different segments of gB2 were tested for human IgG antibody reactivities. The constructs encompassed the amino-proximal protein (gB2 SS2) including amino acids 18 to 228 of gB2, the mid-portion (gB2 AP2) including amino acids 154 to 503 of gB2, and the carboxy-proximal portion (gB2 SS1) including amino acids 228 to 903 of gB2. These recombinant proteins were used as antigen targets in Western immunoblot assays.

Serum samples from 45 individuals with known HSV serotypes by HSV type-specific gG tests were evaluated. gB2 SS2 was strongly reactive with 15 of 15 serum samples from HSV 2+/1− individuals. In contrast, 0 of 15 HSV 1+/2− serum samples, and 0 of 15 HSV 1−/2− serum samples were reactive. GB2 AP2 reactivity was seen in 5 of 15 HSV 2+/1− serum samples, 0 of 15 HSV 1+/2− and 0 of 15 HSV 1−/2− serum samples. Lastly, gB2 SS1 reactivity was seen in 15 of 15 HSV 2+/1− serum samples, 15 of 15 HSV 1+/2− and 0 to 15 HSV 1−2− serum samples.

Thus, HSV gB2 includes an epitope in the aminoproximal region that reacts with HSV-2 antibodies, and an epitope in the carboxy-proximal region that reacts with both HSV-1 and HSV-2 antibodies. These epitopes can be used as type-specific and type-common antigens, respectively, in the present assays.

EXAMPLE 7

Synthesis of a Type-specific gB1 Peptide for Use in HSV Diagnostic Assays

A type-specific gB1 peptide, including amino acids 1–47 of gB1, numbered with reference to the mature molecule (amino acids 31–77, numbered with reference to the precursor molecule), depicted in FIG. 4, was synthesized on an ABI 433A peptide synthesizer (Foster City, Calif.) using a standard 0.25 mM scale and standard ABI FastMoc protocols, chemicals and reagents, as described in Carpino and Han, *J. Amer. Chem. Soc.* (1970) 92:5748–5749; Carpino and Han, *J. Org. Chem.* (1972) 37:3404–3409; and Chang and Meienhofer, *J. Peptide Protein Res.* (1978) 11:246–249. A cysteine residue was added to the N-terminus in order to facilitate conjugation to BSA (see below) and a norleucine residue was added to the C-terminus to aid in determining the amount of peptide conjugated to BSA.

Following synthesis, the peptide was cleaved from the resin support as described in King et al., *Int. J. Peptide Prot. Res.*; and Lundt et al., *Int. J. Peptide Prot. Res.* (1978). The peptide was purified as described in Burke et al. *J. Liq. Chromatogr.* (1988) 11:1229; and Hodges et al., "A Novel Approach to the Purification of Peptides by Reverse-Phase HPLC: Sample Displacement Chromatography," in Peptides: *Chemistry and Biology— Proceedings of the Tenth American Peptide Symposium*, Marshal, Ed., Escom Science Publishers, Leiden, The Netherlands (1988) p. 226. Briefly, reverse phase HPLC was done using a C18 resin and a 45° gradient with 5–50% acetonitrile over 5 column volumes. 0.1% TFA was used as an ion pairing agent. The column eluant was fractionated.

Analytical HPLC was performed on the fractions to test for purity as described in King et al. and Lundt et al., supra. An analytical scale C18 reverse phase column was used with an acetonitrile gradient of 5–50% and 0.1% TEAP as the ion-pairing agent. Fractions of greater than 90% purity were pooled. The final purified peptide pool was 95% pure.

Following synthesis, the peptide was conjugated to BSA (monomeric, Sigma Chemical Co., St. Louis, Mo., catalog number A-1900). Chemical conjugation was performed with Sulfo-SMCC (Pierce, Rockford, Ill.), using standard techniques. See, Brinkley, *Bioconjugate Chem.* (1992) 3:2–13; Hashida et al. *J. Appl. Biochem.* (1984) 6:56–63; and Anjaneyulu and Staros, *International Journal of Peptide and Protein Research* (1987) 30:117–124.

A molar ratio of 4.52 gB1 peptides to one BSA was obtained, as confirmed by standard amino acid analysis techniques by assaying for the presence of norleucine.

After coupling, unbound gB1 peptide was removed from the mixture by diafiltration with an Amicon flow cell using a membrane with a 30,000 molecular weight cutoff. Removal of the free peptide was measured by reverse phase HPLC with an analytical scale column. A gradient from 5–50% acetonitrile was run with 0.1% TEAP as the ion-pairing agent. The area of free peptide to the area of peptide conjugate was compared.

EXAMPLE 8

HSV Diagnostic Assays Using Type-Specific and Type-Common HSV Glycoproteins a. Strip Immunoblot assay (SIA)

Baculovirus-expressed gG1 and gG2 proteins, described above, were applied in discrete narrow bands to nitrocellulose strips at concentrations of 4 µg/ml for gG1 and 0.25 µg/ml for gG2, as the type-specific antigens. The gD2 protein described in Example 4, a type-common protein with an 86% identity between the HSV-1 and HSV-2 homologs, was coated as a further discrete band at a concentration of 1 µg/ml onto the same nitrocellulose strips. As internal controls, additional bands contained purified human IgG at a low (185 ng/ml) and high (925 ng/ml) concentration and anti-human IgM (1 µg/ml).

For the immunoblot assay, strips were processed in a batch fashion with 30 strips per batch. All steps were performed at room temperature. Each strip was numbered and then placed in a separate tube to which was added 1 ml of diluent (PBS with bovine protein stabilizers and detergents, 0.1% sodium azide and 0.05% gentamicin sulfate as preservatives) and 20 µl of a serum sample. The tubes were rocked gently for 4 h, the solution removed by aspiration, and 1 ml of fresh diluent was added to each tube. The tubes were rocked for 30 min, the solution removed by aspiration and 1 ml of wash buffer made from wash buffer concentrate (50×) (phosphate buffered detergent solution with 0.01% thimerosal as a preservative) was added to each tube. The contents of each tube were emptied into a single wash vessel and the strips were washed by swirling for 20 seconds. The wash buffer was decanted and 30 ml of fresh buffer added and the process repeated. Residual solution was removed by aspiration and 20 ml of conjugate solution (peroxidase-labeled goat anti-human IgG (heavy and light chains), with bovine protein stabilizers, containing 0.01% thimerosal as a preservative) was added. The vessel was rotated at 110 rpm for 10 min, the conjugate solution was decanted and the wash step was repeated three times. Residual solution was again removed by aspiration and 20 ml of substrate/developer (4-chloro-1-napthol in methanol/phosphate-buffered hydrogen peroxide) added, followed by rotation for 15–20 min at 110 rpm. The solution was decanted and the strips were washed twice in distilled water. Developed strips were placed face up on paper towels and allowed to dry for 30 min in the dark. Strips were then read within 3 h of drying. The intensity of the color of the HSV antigen bands were assigned values ranging from – (0) to 4+ using the following algorithm. The low IgG band is assigned a value of 1+, the high IgG band is assigned a value of 3+. The gG1, gG2 and gD bands are then scored from 0 to 4+according to how their band intensity compares to that of the IgG control bands.

b. SIA of Random Serum Samples and Comparison of Results to Those Obtained by Western Blot Assay.

A set of 738 randomly chosen serum samples, obtained as screening samples from individuals volunteering for HSV vaccine studies, was analyzed for HSV serostatus using the SIA assay described above. Samples with any of the three HSV antigen bands scoring ≧1+ were considered to be positive. Representative samples showing the various serostatus classes is shown in FIG. 1. The HSV serostatus of each of the samples was also determined separately by Western blot assay according to published procedures. Ashley et al., *J. Clin. Micro.* (1988) 26:662–667.

A comparison of the Immunoblot assay results with the diagnosis obtained from the Western blot assay is shown in Table 1. Of the 327 sera considered to be HSV-1 solely seropositive by the Western blot assay, 286, or 87.5%, were diagnosed by the immunoblot. The 51 samples that gave discordant results for the two assays were distributed into various diagnostic categories; 13 were designated HSV1+ 2+, and 3 were designated as solely HSV2+. Of the 120 sera that were HSV1+2+ by the Western Blot assay, 100 (83.3%) were also detected by immunoblot assay and 20 were determined to be HSV2+ only. A total of 55 samples (12.3% of the total of 447 samples that are HSV1+ or HSV1+2+ by Western blot assay) had no detectable gG1 antibody. Of these, 26 had gD2 antibody only and were designated as positive untypable, 9 were designated as double seronegative and 20 were diagnosed as solely HSV2+. There was an excellent concordance between the two assays for sera designated as only HSV2+ by the Western blot assay, 115 of the 116 (99.1%) were similarly diagnosed by immunoblot assay. Likewise, 174 sera were designated as double seronegative by the immunoblot assay corresponding to 98.9% of the 176 sera so designated by the Western blot assay.

TABLE 1

SIA HSV-1 and HSV-2 Results
Compared with 738 serum samples characterized by Western Blot

| Western: | SIA: HSV-1 positive | HSV-1&2 positive | HSV-2 positive | Positive-Untypable | HSV-1&2 Negative |
|---|---|---|---|---|---|
| HSV-1 positive | 286/327 | 2/327 | 3/327 | 26/327 | 9/327 |
|  | (87.5%) | (0.6%) | (0.9%) | (0.8%) | (2.7%) |
| HSV-1&2 positive | 0/120 | 100/120 | 20/120 | 0/120 | 0/120 |
|  |  | (83.3%) | (16.7%) |  |  |
| HSV-2 positive | 0/116 | 0/116 | 115/116 | 1/116 | 0/116 |
|  |  |  | (99.1%) | (0.8%) |  |
| HSV-1&2 Negative | 0/176 | 0/176 | 0/176 | 2/176 | 174/176 |
|  |  |  |  | (1.1%) | (98.9%) | c. SIA of Random Serum Samples and Comparison of Results to Those Obtained by Western Blot Assay Using a Type-specific gB1 peptide Type-specific gG1 and gG2 produced in yeast and described in Examples 1a and 2b (C-terminal region), respectively, and the type-common gD2 protein described in Example 4, were applied to nitrocellulose strips as described in Example 8a. Additionally, the synthetic type-specific gB1-BSA peptide, described in Example 7, was applied as a discrete narrow band to nitrocellulose strips at a concentration of 1 μg/ml. As internal controls, additional bands contained purified human IgG at a low (185 ng/ml) and high (925 ng/ml) concentration and anti-human IgM (1 μg/ml).

737 randomly selected sera from healthy adults, 18–50 yrs., were screened using this SIA to determine HSV serostatus (Table 2). Of these, 176 (23.9%) had no antibody to HSV, 419 (56.8%) were HSV-1 seropositive, 243 (33.0%) were HSV-2 seropositive and a subset of 122 were dual HSV-1 and –2 seropositive. An additional 21 had only gD2 antibody and thus were designated as HSV seropositive, untypable. When these diagnoses were compared to those determined by the Western blot (WB) assay, the SIA correctly identified 92.4% of HSV-1 positive, 99.6% of HSV-2 positive and 97.1% of HSV negative samples.

The gB1 peptide diagnosed 264 (88.9%) of a total of 297 sera designated by SIA as HSV-1 solely seropositive compared to the gG1 protein that diagnosed 260/297 (87.5%) (Table 3). Thus, the gB1 peptide was as good an antigen for this purpose as the gG1 protein. Of the 122 sera designated as HSV-1$^+$/HSV-2$^+$ by SIA, the gB1 peptide detected 101/122 or 82.8% compared to 108/122 (88.5%) detected by the gG1 protein. Of the 419 sera diagnosed as HSV-1$^+$/2$^+$ by SIA, 414 concurred with the Western blot diagnosis. The gB1 peptide diagnosed 3 sera as HSV-1$^+$/2$^+$ that were HSV-2$^+$ only by Western blot analysis (corresponding to 3 HSV-1 false positives). The gG1 protein diagnosed 1 serum as HSV-1$^+$/2$^+$ that by Western blot was HSV-2$^+$ only giving a total of 4/419 (0.95%) HSV-1 false positives combining results from both antigens. Thus, 415/449 (92.4%) HSV-1$^+$ samples by Western blot were correctly diagnosed by SIA. Both gB1 and gG1 antigens contributed equally to the final HSV-1$^+$ diagnosis. Thus, the final algorithm for reading the SIA is that if either or both of the gB1 and the gG1 antigen bands are positive, the sera is HSV-1$^+$. Of the 34 HSV-1$^+$ sera by Western blot that were HSV-1[31] by SIA, 12 were designated as HSV-2$^+$ only, 6 were designated as HSV negative and 16 as HSV positive, untypable. The addition of the gB1 peptide to the SIA assay reduced the number of HSV-1 false negatives by about 50% compared to an assay including only gG1 as the HSV-1 specific antigen 82.0% (–gB1) to 93.3% (+gB1).

The ease of performance and the wider availability of the HSV SIA compared to the HSV Western blot assay may facilitate widespread serological screening for HSV.

TABLE 2

| WB Diagnosis | N | SIA Diagnosis | N | % Correct by SIA Compared to WB |
|---|---|---|---|---|
| HSV negative | 175 | HSV negative | 170 | 97.7 |
|  |  | Pos./Untyp. | 5 |  |
| HSV-1$^+$ | 330 | HSV-1$^+$ | 296 | 89.7 |
|  |  | HSV-2$^+$ | 1 |  |
|  |  | HSV-1$^+$/2$^+$ | 11 |  |
|  |  | HSV neg. | 6 |  |
|  |  | Pos./Untyp. | 16 |  |
| HSV-2$^+$ | 113 | HSV-2$^+$ | 109 | 96.5 |
|  |  | HSV-1$^+$/2$^+$ | 4 |  |
| HSV-1$^+$/2$^+$ | 119 | HSV-1$^+$/2$^+$ | 107 | 89.9 |
|  |  | HSV-1$^+$ | 1 |  |
|  |  | HSV-2$^+$ | 11 |  |

TABLE 3

| SIA Diagnosis | gB1 positive | gG1 positive | Both positive | Neither positive | Total HSV-1 positive |
|---|---|---|---|---|---|
| HSV-1$^+$ | 37 | 33 | 227 | — | 297 |
| HSV-1$^+$ and HSV-2$^+$ | 14* | 21** | 87 | — | 122 |
| HSV negative | 1† | 2† | — | — | 0 |
| Positive, Untypable | 0 | 0 | 0 | 20 | 0 |
| HSV-2$^+$ | 0 | 0 | 0 | 0 | 0 |

*3 of these are HSV-2$^+$ only by WB;
**1 of these is HSV-2$^+$ only by WB.
†These were diagnosed as HSV negative since gD2 was negative.

d. ELISA

A gG ELISA method was carried out using the following steps. An Immulon 2 microtiter plate (available from Dynatech Laboratories, Chantilly, Va.) was coated with gG1 or gG2 antigen by application of the respective antigen in borate buffer to the plates at 2 μg/ml (50 λ/well) overnight at 4° C. The plates were washed four times with a wash buffer comprising 0.14M NaCl and 0.05% Triton X-100, and the plates were blocked with 10% Fetal calf serum (FCS), 0.3% Tween 20 in phosphate buffered saline (PBS) for approximately two hours at 37° C. The plates were washed four times with a suitable wash, and human sera, diluted 1:20 in dilution solution including 0.25M sodium phosphate dibasic, 0.001M EDTA, 0.5M NaCl, 0.2M Thimerosal, 0.01% Triton X-100, 0.001% HCl, 6N, and 1% Casein. Samples were added at 50 λ/well and the plates incubated at 37° C. for approximately 2 hours.

After reaction with the human sera, the plates were washed four times, and Cappel Fab'2 goat anti-human IgG conjugated to horseradish peroxidase (HRP) (diluted 1:4000 in dilution solution (at 50 λ/well) was added to the wells and incubated at 37° C. for approximately 1 hour. After washing four times with a suitable wash solution, the plates were developed for approximately 15 minutes with OPD (o-Phenylenediamine Dihydrochloride) solution added at 50 λ/well. The reaction was stopped with 4N H$_2$SO$_4$ (added at 50 λ/well), and the plates read in an ELISA reader ar OD 490–650. The results of the assays are depicted below in Tables 4 and 5.

TABLE 4 gG1 Assay Results

|  | False + | False – | % Error |
|---|---|---|---|
| Before gD | 16/559 (2.9%) | 16/559 (2.9%) | 5.7% |
| After gD | 6/559 (1.1%) | 16/559 (2.9%) | 3.9% |

TABLE 5 gG2 Assay Results

|  | False + | False – | % Error |
|---|---|---|---|
| Before gD | 11/559 (2.0%) | 11/559 (2.0%) | 3.9% |
| After gD | 10/559 (1.8%) | 11/559 (2.0%) | 3.8% |

Thus, novel methods for detecting HSV infection are disclosed. Although preferred embodiments of the subject invention have been described in some detail, it is understood that obvious variations can be made without departing from the spirit and the scope of the invention as defined by the appended claims.

We claim:

1. A method of detecting the presence of antibodies to herpes simplex virus (HSV) comprising:
(a) providing a biological sample from a human suspected of containing antibodies to HSV type 1 (HSV-1) and/or HSV type 2 (HSV-2);
(b) contacting said biological sample with one or more purified type-specific HSV-1 polypeptides bound to a solid support, one or more purified type specific HSV-2 polypeptides bound to a solid support, and one or more purified type-common HSV polypeptides bound to a solid support, under conditions which allow HSV antibodies, when present in the biological sample, to bind to said type-specific and/or said type-common polypeptides; and
(c) detecting the presence or absence of bound antibodies from step (b) as an indication of the presence or absence of HSV, wherein said detecting is done using one or more detectably labeled anti-human immunoglobulin antibodies.

2. The method of claim 1, wherein said HSV is HSV-1.

3. The method of claim 1, wherein said HSV is HSV-2.

4. The method of claim 1 wherein the detectable label is a fluorescer or an enzyme.

5. The method of claim 1 wherein the solid support is a nitrocellulose strip.

6. The method of claim 1, wherein said type-specific HSV-1 polypeptide and/or said type-specific HSV-2 polypeptide is an HSV glycoprotein G (gG) polypeptide.

7. The method of claim 6, wherein said gG polypeptide is a gG1 polypeptide.

8. The method of claim 6, wherein said gG polypeptide is a gG2 polypeptide.

9. The method of claim 6, wherein said type-specific HSV-1 polypeptide is an HSV gG1 polypeptide and said type-specific HSV-2 polypeptide is an HSV gG2 polypeptide.

10. The method of claim 6, wherein said gG polypeptide has all or a part of a transmembrane domain deleted therefrom.

11. The method of claim 1, wherein said type-specific HSV-1 polypeptide is a type-specific epitope of HSV-1 glycoprotein B (gB1) comprising an amino acid sequence corresponding to amino acids 1–47 of HSV gB1, numbered with reference to the mature gB1 molecule.

12. The method of claim 1, wherein said one or more type-common polypeptides comprises an HSV glycoprotein D (gD) polypeptide.

13. The method of claim 12, wherein said gD polypeptide is a gD1 polypeptide.

14. The method of claim 12, wherein said gD polypeptide is a gD2 polypeptide.

15. The method of claim 12, wherein said gD polypeptide has all or a part of a transmembrane domain deleted therefrom.

16. The method of claim 1, wherein said one or more type-common polypeptides comprises an HSV glycoprotein B (gB) polypeptide.

17. The method of claim 16, wherein said gB polypeptide is a gB1 polypeptide.

18. The method of claim 16, wherein said gB polypeptide is a gB2 polypeptide.

19. The method of claim 16, wherein said gB polypeptide has all or a part of a transmembrane domain deleted therefrom.

20. The method of claim 1, wherein said one or more type-common polypeptides comprises an HSV VP16 polypeptide.

21. The method of claim 20, wherein said VP16 polypeptide is an HSV-1 VP16 polypeptide.

22. The method of claim 20, wherein said VP16 polypeptide is an HSV-2 VP16 polypeptide.

23. The method of claim 1, wherein said biological sample is a human serum sample.

24. A method for distinguishing between herpes simplex virus type 1 (HSV-1) and herpes simplex virus type 2 (HSV-2) in a human serum sample suspected of containing antibodies to HSV-1 and/or HSV-2, said method comprising:
(a) immobilizing one or more purified type-specific HSV-1 polypeptides, one or more purified type-specific HSV-2 polypeptides and one or more purified type-common HSV polypeptides in discrete positions on a nitrocellulose strip, wherein said one or more purified type-specific HSV-1 polypeptides are selected from the group consisting of an HSV-1 glycoprotein G (gG1) polypeptide and a type-specific epitope of HSV-1 glycoprotein B (gB1) comprising an amino acid sequence corresponding to amino acids 1–47 of HSV gB1, numbered with reference to the mature gB1 molecule, and further wherein said one or more purified type-specific HSV-2 polypeptides comprise a type-specific HSV-2 glycoprotein G (gG2) polypeptide;
(b) contacting said nitrocellulose strip from step (a) with said human serum sample under conditions which allow anti-HSV-1 and anti-HSV-2 antibodies, when present in the biological sample, to bind to said type-specific and/or said type-common HSV polypeptides;
(c) contacting a detectably labeled anti-human immunoglobulin antibody with bound antibodies of step (b) to form labeled antibody/anti-human immunoglobulin antibody complexes; and
(d) detecting the labeled complexes of step (c),
thereby distinguishing between HSV-1 and HSV-2 in said biological sample.

25. The method of claim 24, wherein said one or more type-common HSV polypeptides comprises a type-common HSV-1 glycoprotein D (gD1) polypeptide.

26. The method of claim 24, wherein said one or more type-common HSV polypeptides comprises a type-common HSV-2 glycoprotein D (gD2) polypeptide.

27. The method of claim 24, wherein said one or more type-common HSV polypeptides comprises a type-common HSV-1 glycoprotein B (gB1) polypeptide.

28. The method of claim 24, wherein said one or more type-common HSV polypeptides comprises a type-common HSV-2 glycoprotein B (gB2) polypeptide.

29. The method of claim 24, wherein said one or more type-common HSV polypeptides comprises a type-common HSV-1 VP16 polypeptide.

30. The method of claim 24, wherein said one or more type-common HSV polypeptides comprises a type-common HSV-2 VP16 polypeptide.

31. The method of claim 24, wherein said gG1, gG2 and type-common HSV polypeptides have all or a part of a transmembrane domain deleted therefrom.

32. An immunodiagnostic test kit for detecting herpes simplex virus (HSV) antibodies in a human serum sample, said test kit comprising one or more purified type-specific HSV type 1 (HSV-1) polypeptides bound to a solid support wherein said one or more purified type-specific HSV-1 polypeptides are selected from the group consisting of an HSV-1 glycoprotein G (gG1) polypeptide and a type-specific epitope of HSV-1 glycoprotein B (gB1) comprising an amino acid sequence corresponding to amino acids 1–47 of HSV gB1, numbered with reference to the mature gB1 molecule, a purified type-specific HSV type 2 (HSV-2) polypeptide bound to a solid support wherein said purified type-specific HSV-2 polypeptide is an HSV-2 glycoprotein G (gG2) polypeptide, and one or more purified type-common HSV polypeptides bound to a solid support, and instructions for conducting the immunodiagnostic test.

33. The immunodiagnostic test kit of claim 32, wherein said type-specific HSV-1 polypeptide is an HSV gG1 polypeptide and said type-specific HSV-2 polypeptide is an HSV gG2 polypeptide.

34. The immunodiagnostic test kit of claim 32, wherein said gG polypeptide has all or a part of a transmembrane domain deleted therefrom.

35. The immunodiagnostic test kit of claim 32, wherein said type-specific HSV-1 polypeptide is a type-specific epitope of HSV-1 glycoprotein B (gB1) comprising an amino acid sequence corresponding to amino acids 1–47 of HSV gB1, numbered with reference to the mature gB1 molecule.

36. The immunodiagnostic test kit of claim 32, wherein said one or more type-common polypeptides comprises an HSV glycoprotein D (gD) polypeptide.

37. The immunodiagnostic test kit of claim 36, wherein said gD polypeptide is a gD1 polypeptide.

38. The immunodiagnostic test kit of claim 36, wherein said gD polypeptide is a gD2 polypeptide.

39. The immunodiagnostic test kit of claim 36, wherein said gD polypeptide has all or a part of a transmembrane domain deleted therefrom.

40. The immunodiagnostic test kit of claim 32, wherein said one or more type-common polypeptides comprises an HSV glycoprotein B (gB) polypeptide.

41. The immunodiagnostic test kit of claim 40, wherein said gB polypeptide is a gB1 polypeptide.

42. The immunodiagnostic test kit of claim 40, wherein said gB polypeptide is a gB2 polypeptide.

43. The immunodiagnostic test kit of claim 40, wherein said gB polypeptide has all or a part of a transmembrane domain deleted therefrom.

44. The immunodiagnostic test kit of claim 32, wherein said one or more type-common polypeptides comprises an HSV VP16 polypeptide.

45. The immunodiagnostic test kit of claim 44, wherein said VP16 polypeptide is an HSV-1 VP16 polypeptide.

46. The immunodiagnostic test kit of claim 44, wherein said VP16 polypeptide is an HSV-2 VP16 polypeptide.

* * * * *

```
                           SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ala Pro Ser Ser Pro Gly Thr Pro Gly Val Ala Ala Ala Thr Gln Ala
    1               5                  10                  15

Ala Asn Gly Gly Pro Ala Thr Pro Ala Pro Pro Ala Leu Gly Ala Ala
                20                  25                  30

Pro Thr Gly Asp Pro Lys Pro Lys Lys Asn Lys Lys Pro Lys
            35                  40                  45

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Glu Glu Glu Glu Gly Ala Gly Asp Gly Glu
    1               5                  10

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Glu Glu Phe Glu Gly Ala Gly Asp Gly Leu
    1               5                  10

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Pro Ala Arg Pro Glu Thr Ser Arg Pro Lys Thr Pro Pro Thr Ser Ile
    1               5                  10                  15
```

```
        Ile Gly Pro Leu Ala
                    20
```

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
        Pro Ala Arg Pro Gly Ala Ile Arg Pro Thr Leu Pro Pro Gly Ile Leu
        1               5                   10                  15

Gly Pro Leu Ala
                    20
```

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
        Pro Thr Pro Gln His Thr Pro Leu Phe Ser Phe Leu Thr Ala Ser Pro
        1               5                   10                  15

Ala Leu Asp
```

(2) INFORMATION FOR SEQ ID NO:7:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
        Pro Thr Pro Gln His Ile Pro Leu Phe Trp Phe Leu Thr Ala Ser Pro
        1               5                   10                  15

Ala Leu Asp
```

(2) INFORMATION FOR SEQ ID NO:8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
AGGAACCATG GCAATGTCGC CGGGCGCCAT GCTGGCCGTT GTT                              43
```

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:9:

TCCCGTCGAC TACTAGTCCA GGGCGGGGGA GGCAGTGAGG AACGA                45

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGTACCGGAT CCCTGCAGAT GTCGCAGGGC GCCATGCGTG                      40

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TTATCAGGAT CCCTATTCCA TTGGCATGTA TTCGTCCAGG GCGGGGAGG CAGT        54

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TTCCATTGGC ATGTATTC                                              18

(2) INFORMATION FOR SEQ ID NO:13:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AGTACCGGAT CCCTGCAGAT GCACGCCATC GCTCCCAGG                       39

(2) INFORMATION FOR SEQ ID NO:14:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
TTATCAGGAT CCCTATTCCA TTGGCATGTA TTCATCTAGA GCAGGGGAGG CCG              53
```

(2) INFORMATION FOR SEQ ID NO:15:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
AACTGCAGAA ATGCTGGGGC CCTGCATGCT GCTGCTGCTG CTGCTGCTGG GCCTGAGGCT       60

ACAGCTCTCC CTGGGCATCG CCTTGACCGA GGACGCGTCC TCCGAT                    106
```

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
AGGGCGCCAT GGCGGTGGCC GACA                                             24
```

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GATAACCATC TCGCAAATAA ATAAG                                            25
```

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CATCTCGTCG GGGGAGTAG T                                                 21
```

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
ACAGATCTTA TGGACCTGTT GGTCGAC                                          27
```

-continued (2) INFORMATION FOR SEQ ID NO:20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AGAATTCACT ATTCCATTGG CATGTATTCG GTGGACAGTC TGCG        44